United States Patent
Lanes et al.

(10) Patent No.: US 9,422,595 B2
(45) Date of Patent: Aug. 23, 2016

(54) ENDONUCLEASES

(71) Applicant: Biotec Pharmacon ASA, Tromsø (NO)

(72) Inventors: Olav Lanes, Tromsø (NO); Linda Havdalen, Tromsø (NO); Terese Solstad, Kvaløysletta (NO); Marit Lorentzen, Krokelvdalen (NO); Bjørn Altermark, Tromsø (NO); Ingar Leiros, Tromsø (NO); Ronny Helland, Tromsdalen (NO)

(73) Assignee: BIOTEC PHARMACON ASA, Tromsø (NO)

( * ) Notice: Subject to any disclaimer, the term of this patent is extended or adjusted under 35 U.S.C. 154(b) by 77 days.

(21) Appl. No.: 14/377,013

(22) PCT Filed: Feb. 18, 2013

(86) PCT No.: PCT/GB2013/050387
§ 371 (c)(1),
(2) Date: Aug. 6, 2014

(87) PCT Pub. No.: WO2013/121228
PCT Pub. Date: Aug. 22, 2013

(65) Prior Publication Data
US 2014/0370514 A1 Dec. 18, 2014

(30) Foreign Application Priority Data

Feb. 17, 2012 (GB) .................................. 1202768.6
Sep. 7, 2012 (GB) .................................. 1216029.7

(51) Int. Cl.
*C12Q 1/00* (2006.01)
*C12N 9/00* (2006.01)
*C12Q 1/68* (2006.01)
*C12N 9/22* (2006.01)

(52) U.S. Cl.
CPC .............. *C12Q 1/6806* (2013.01); *C12N 9/22* (2013.01); *C12Y 301/21001* (2013.01); *C12Q 2521/301* (2013.01)

(58) Field of Classification Search
CPC ................................... C12Q 1/00; C12N 9/00
USPC ........................................ 435/183, 6; 530/350
See application file for complete search history.

(56) References Cited

U.S. PATENT DOCUMENTS

| | | | |
|---|---|---|---|
| 5,006,472 | A | 4/1991 | Dove et al. |
| 7,893,251 | B2 | 2/2011 | Lorenz |
| 2002/0172972 | A1 | 11/2002 | Tabor et al. |
| 2008/0160528 | A1 | 7/2008 | Lorenz |
| 2009/0047705 | A1 | 2/2009 | Awazu et al. |
| 2011/0195486 | A1 | 8/2011 | Liu et al. |

FOREIGN PATENT DOCUMENTS

| | | |
|---|---|---|
| WO | 99/007887 A2 | 2/1999 |
| WO | 2007/143206 A2 | 12/2007 |
| WO | 2011010094 A1 | 1/2011 |

OTHER PUBLICATIONS

Database UniProt [Online] Jan. 19, 2010, SubName: Full=Endonuclease I; XP002694179, retrieved from EBI accession No. UNIPROT:D0YWJ5 Database accession No. D0YWJ5 sequence.
Database UniProt [Online] May 3, 2011, "SubName: Full=Extracellular deoxyribonuclease;", XP002694180, retrieved from EBI accession No. F0LWL3 sequence.
Database UniProt [Online] Feb. 6, 2013, "SubName: Full=Extracellular deoxyribonuclease Dns; EC=3.1.21.-;", XP002694181, retrieved from EBI accession No. UNIPROT:K8B9T0 Database accession No. K8B9TO sequence.
Veronika E. Anisimova et al: "Thermolabile duplex-specific nuclease", Biotechnology Letters, Springer Netherlands, Dordrecht, vol. 31, No. 2, Sep. 23, 2008, pp. 251-257.
Bjorn Altermark et al: "Structural adaptation of endonuclease I from the cold-adapted and halophilic bacterium Vibrio salmonicida", Acta Crystallographica Section D Biological Crystallography, vol. 64, No. 4, Apr. 1, 2008, pp. 368-376.
Database NCBI Accession No. ACI06978.1 Fouts et al. (2008).
Niiranen et al., "Effects of salt on the kinetics and thermodynamic stability of endonuclease I from Vibrio salmonicida and Vibrio cholerae," FEBS Journal 275: 1593-1605 (2008).
Altermark et al., "Comparative studies of endonuclease I from cold-adapted Vibrio salmonicida and mesophilic Vibrio cholerae," FEBS Journal 274: 252-263 (2007).
Altermark et al., "Structural adaptation of endonuclease I from the cold-adapted and halophilic bacterium Virio salmonicida," A Acta Crystallographica D: Biological Crystallography 64: 368-376 (2008).
Altermark et al., "The structure of Vibrio cholerae extracellular endonuclease I reveals the presence of a buried chloride ion," A Acta Crystallographica D: Biological Crystallography 62: 1387-1391 (2006).
Database UniProt [Online] Jan. 19, 2010 Database accession No. D0YWJ5.
Database UniProt [Online] May 3, 2011 Database accession No. F0LWL3.
Database UniProt [Online] Feb. 6, 2013 Database accession No. K8B9TO.
Altermark et al., "Sequence comparison and environmental adaptation of a bactrial endonuclease," Computational Biology and Chemistry 31: 163-172 (2007).
Altermark et al., (2006) Poster at BIOPROSP 2006, Symposium in marine bioprospecting. Tromsø, Norway. Oct. 11-12, 2006.
Altermark et al., (2006) Abstract for Poster at BIOPROSP 2006, Symposium in marine bioprospecting. Tromsø, Norway. Oct. 11-12, 2006.
International Search Report for PCT/GB2013/050387 dated Apr. 8, 2013, 5 pages.

*Primary Examiner* — Maryam Monshipouri
(74) *Attorney, Agent, or Firm* — Rothwell, Figg, Ernst & Manbeck, P.C.

(57) ABSTRACT

The present invention provides an endonuclease I or enzymatically active fragment thereof wherein said endonuclease I has the sequence of SEQ ID No. 4 or a sequence which is at least 70% identical thereto and wherein the amino acid residue which is immediately N-terminal of the FYCGC pentapeptide motif has been substituted with a residue which is negatively charged as well as nucleic acid molecules encoding these enzymes and methods of removing contaminating polynucleotides from a sample using these enzyme.

21 Claims, 19 Drawing Sheets

Figure 1

```
VsEndA      MKLIRLVISLIAVSFTVNVMAAPPSSFSKAKKEAVKIYLDYPTSFYCGCDITWKNKKKGI  60
VcEndA      MMIFRFVTT-LAASLPLLTFAAP-ISFSHAKNEAVKIYRDHPVSFYCGCEIRWQGKK-GI  57
              * *    * *           *** *** ** ****** * * ****** * *  ** **

VsEndA      PELESCGYQVRKQEKRASRIEWEHVVPAWQFGHQRQCWQKGGRKNCTRNDKQFKSMEADL 120
VcEndA      PDLESCCYQVRKNENRASRIEWEHVVPAWQFGHQLQCWQQCGRKNCTRTSPEFNQMEADL 117
            * ******** * ***************** **** * ********  *   *****

VsEndA      HNLVPAIGEVNGDRSNFRFSQWNGSKGAFYGQCAFKVDFKGRVAEPPAQSRGAIARTYLY 180
VcEndA      HNLTPAIGEVNGNRSNFSFSQWNGIDGVTYGQCEMQVNFKERTAMPPERARGAIARTYLY 177
            *** ******** **** ******    * ****   * ** ** *  *  **********

VsEndA      MNNEYKFNLSKAQRQLMEAWNKQYPVSTWECTRDERIAKIQGNHNQFVYKACTK 234
VcEndA      MSEQYGLRLSKAQNQLMQAWNNQYPVSEWECVRDQKIEKVQGNSNRFVREQCPN 231
            *  *   * ***** *** *** **** *** **  *  *** *  **   * 
```

Figure 2

```
1     ATG AAA TTA ATT CGC TTA GTT ATC AGT CTT ATT GCT GTC AGT TTC   45
1      M   K   L   I   R   L   V   I   S   L   I   A   V   S   F    15

46    ACT GTT AAC GTA ATG GCA GCA CCT CCT TCT TCT TTC TCA AAA GCA   90
16     T   V   N   V   M   A   A   P   P   S   S   F   S   K   A    30

91    AAA AAA GAA GCC GTC AAA ATC TAT CTT GAT TAC CCA ACC GAG TTT   135
31     K   K   E   A   V   K   I   Y   L   D   Y   P   T   E   F    45

136   TAT TGT GGC TGT GAC ATT ACG TGG AAA AAT AAA AAG AAA GGG ATC   180
46     Y   C   G   C   D   I   T   W   K   N   K   K   K   G   I    60

181   CCT GAA TTA GAA AGC TGC GGA TAC CAA GTC CGT AAA CAA GAA AAA   225
61     P   E   L   E   S   C   G   Y   Q   V   R   K   Q   E   K    75

226   CGA GCC AGT CGT ATT GAA TGG GAG CAT GTT GTT CCA GCA TGG CAA   270
76     R   A   S   R   I   E   W   E   H   V   V   P   A   W   Q    90

271   TTT GGT CAT CAA CGT CAA TGT TGG CAA AAA GGT GGG CGT AAA AAT   315
91     F   G   H   Q   R   Q   C   W   Q   K   G   G   R   K   N    105

316   TGC ACT AGA AAC GAC AAG CAA TTC AAA TCA ATG GAA GCC GAC TTA   360
106    C   T   R   N   D   K   Q   F   K   S   M   E   A   D   L    120

361   CAT AAT CTA GTG CCT GCG ATT GGT GAA GTA AAC GGG GAC AGA TCC   405
121    H   N   L   V   P   A   I   G   E   V   N   G   D   R   S    135

406   AAC TTC CGA TTC TCA CAA TGG AAT GGA AGC AAA GGC GCT TTC TAT   450
136    N   F   R   F   S   Q   W   N   G   S   K   G   A   F   Y    150

451   GGC CAA TGT GCT TTT AAA GTC GAC TTC AAA GGC CGT GTT GCC GAG   495
151    G   Q   C   A   F   K   V   D   F   K   G   R   V   A   E    165

496   CCA CCA GCA CAA TCT CGT GGT GCC ATT GCC CGA ACG TAT CTT TAT   540
166    P   P   A   Q   S   R   G   A   I   A   R   T   Y   L   Y    180

541   ATG AAC AAC GAA TAT AAA TTT AAC TTA TCA AAA GCA CAG CGA CAA   585
181    M   N   N   E   Y   K   F   N   L   S   K   A   Q   R   Q    195

586   CTT ATG GAA GCA TGG AAC AAA CAG TAT CCA GTA TCA ACT TGG GAA   630
196    L   M   E   A   W   N   K   Q   Y   P   V   S   T   W   E    210

631   TGT ACT CGT GAT GAA CGT ATA GCA AAA ATC CAA GGC AAT CAT AAT   675
211    C   T   R   D   E   R   I   A   K   I   Q   G   N   H   N    225

676   CAA TTT GTT TAT AAA GCA TGC ACT AAA TAA   705
226    Q   F   V   Y   K   A   C   T   K   *
```

Figure 3

```
                                                                    ↓
V.salmonicida    ------------AP--PSSFSKAKKEAVKIYLDYPT------SFYCGCDITWKNKKKGIP 40
V.cholerae       ------------A--PISFSHAKNEAVKIYRDHPV------SFYCCCEIRWQCKK-CIP 38
Oceanimonas sp.  ------------GE--AMSFRQAKKVAPGIYNDNLK------TFYCGCNIDTQGKK-LVP 39
Salmonella sp.               DG  INNFSQAKAASVKVNADAPG        SFYCGCQIRWQGKK GVV 39
Enterobacter sp.------------DG--INSFSQAKAAGVKVNADVPG------DFYCGCKINWQGKK-GIV 39
Yokenella sp.    ------------EG--INSFSQAKAAGVKVNADVAG------DFYCGCKINWQGKK-GVV 39
Klebsiella sp.               AG  INSFSQAKAAGVKVNADVPG        DFYCGCKIDWQGKK GVI 39
E.coli           ------------EG--INSFSQAKAVAVKIHADAPG------TFYCGCKIDWQGKK-GVV 39
Shigella sp.     ------------EG--INSFSQAKAAAVKVHADAPG------TFYCGCKINWQGKK-GVV 39
Citrobacter sp.  ------------EG--INSFSQAKAAGVKVNADAPG------DFYCCCKINWQCKK-GVV 39
Cronobacter sp.  ------------ASG--HSFSQAKAAGVKINADAPG------DFYCGCPITWQGKK-GIP 40
Rahnella sp.     ICALVPLSAFSQSGNTINNFSQAKAAAVKINQCAP        TFYCCCNIRWQCKK CTP 52
Erwinia sp.      -FPPLFCHALSQGNYQQNNFSQAKAWAAQIHHDAPG------TFYCGCKIDWQGKK-GVP 52
Yersinia sp.     ------------HG---NNFSQAKAVAAKIIQDAPG------SFYCGCQIDWQGKK-GIP 39
Serratia sp.     ------------HG--INNFSQAKAAAAKINQDAPG------SFYCCCKINWHCKK-GLP 39
Pseudomonas sp.  ------------AQAQAPRTFSEAKKVAWGLYAPQST------EFYCGCKY--TGKR---V 38
                              *   **                       *****     *

V.salmonicida    ELESCCGYQVRKQEKRASRIEWEHVVPAWQFGHQRQCWQKCCRKNCTRNDKQFKSMEADLH 100
V.cholerae sp.   DLESCGYQVRKNENRASRIEWEHVVPAWQFGHQLQCWQQGGRKNCTRTSPEFNQMEADLH 98
Oceanimonas sp.  DLAGCGYQVRKQQQRASRIEWEHVVPAWIFGHQRQCWQQGGRKNCTRKDELFRQMEGDLH 99
Salmonella sp.   DLESCGYKVRKNENRARRIEWEHVVPAWQFGHQRQCWQDGGRKNCAK-DPVYRKMESDMH 98
Enterobacter sp. DLESCGYKVRKNENRASRIEWEHVVPAWQFGHQRQCWQDGGRKNCAK DPVYRQMESDMH 98
Yokenella sp.    DLESCCGYKVRKNENRASRIEWEHVVPAWQFGHQRQCCRKNCCK-DPVYRQMESDMH 98
Klebsiella sp.   DLESCGYKVRKNENRASRVEWEHVVPAWQFGHQRQCWQEGGRKNCAK-DPEYRKMESDMH 98
E.coli           DLQSCGYQVRKNENRASRVEWEHVVPAWQFGHQRQCWQGGRKNCAK-DPVYRKMESDMH 98
Shigella sp.     DLQSCGYQVRKNENRASRVEWEHVVPAWQFGHQRQCWQDGGRKNCAK DPVYRKMESDMH 98
Citrobacter sp.  DLESCCGYKVRKNENRASRIEWEHVVPAWQFGHQRQCWQDCCRKNCAK-DPVYRKMESDMH 98
Cronobacter sp.  DLKACGYQVRKNENRASRIEWEHVVPAWQFGHQRQCWQNGGRKNCDK-DPVYREMETDLH 99
Rahnella sp.     DLQSCGYAVRKSELRASRIEWEHVVPAWQFGHQMQCWQDGGRKNCAK-NADYRQVETDLH 111
Erwinia sp.      DLTSCGYQVRKNSERASRIEWEHVVPAWSFGHQRQCWQDGGRKNCVK-DPVYRRMESDLH 111
Yersinia sp.     DLNSCCGYQPRKNAARAARIEWEHVVPAWQFGHQRQCWQQCCRKNCAK-DPVYRQIETDLH 98
Serratia sp.     DLNACGYQPRKNAQRAGRIEWEHVVPAWQFGHQLQCWQDGGRKNCNR-DPVYRQIETDLH 98
Pseudomonas sp.  DLAGCGYVPRKSAKRASRIEWEHIVPAWQIGHLRQCWQNGGRKNCTKSDPVYKRAEADLH 98
                    ***  **    ** * ****  ****  **    ****  ******       * * *

V.salmonicida    NLVPAIGEVNCDRSNFRFSQWNCSKGAFYGQCAFKVDFKGRVAEPPAQSRGAIARTYLYM 160
V.cholerae       NLTPAIGEVNGNRSNFSFSQWNGIDGVTYGQCEMQVNFKERIAMPPERARGAIARTYLYM 158
Oceanimonas sp.  NLVPAVGEVNGDRSNYRFSEWNG-KPVQYGQCQMLVDFKGRKVQPPEQSRGAIARTYLYM 158
Salmonella sp.   NLQPAIGEVNGDRGNFMYSQWNG-GEGQYGQCAMKVDFKAKLAEPPARARGAIARTYFYM 157
Enterobacter sp. NLQPAVGEVNGDRGNFMYSQWNG GEGQYGQCGMKVDFKEKVAEPPARARGSIARTYFYM 157
Yokenella sp.    NLQPAVGEVNGDRGNFMYSQWNG-GEGQYGQCAMKVDFKGKVAEPPARARGAIARTYFYM 157
Klebsiella sp.   NLQPAVGEVNGDRGNFMYSQWNG-GEGQYGQCTMKVDFKDKIAEPPARARGAIARTYFYM 157
E.coli           NLQPSVGEVNGDRGNFMYSQWNG-GEGQYGQCAMKVDFKEKVAEPPARARGAIARTYFYM 157
Shigella sp.     NLQPSVCEVNGDRGNFMYSQWNG GEGQYGQCAMKVDFKEKAAEPPARARGAIARTYFYM 157
Citrobacter sp.  NLQPAVGEVNGDRANFMYSQWNG-GEGQYGQCAMKVDFKEKVAEPPARARGAIARTYFYM 157
Cronobacter sp.  NLQPAVGEVNGDRGNFLYSQWRG-GEGQYGQCEMKVDFKNKQAEPPARARGAIARTYFYM 158
Rahnella sp.     NLEPAIGEVNGDRNNFMYSQWNG-GEGQYGRCEMKIDFKAKAAEPPARARGAIARTYFYM 170
Erwinia sp.      NLQPAIGEVNGDRCNFMYCQWNG-GEQQYCQCAMKVDFKNKLAEPPARARGAIARTWFYM 170
Yersinia sp.     NLQPAIGEVNGDRNNFMYSQWNG-GSGQYGQCAMKVDFKNKLAEPPVRARGAIARTYFYM 157
Serratia sp.     NLQPAIGEVNGDRNNFMYSQWRG-GEGQYGQCPMKVDFKHKQAEPPARARGAIARTYFYM 157
Pseudomonas sp.  NLVPSIGEVNGDRSNFSFGWVPE-QKGQYGSCLIQVDFKAKKVMPRPSIRGMIARTYFYM 157
                 **  *  *****  *            ** *       **       *   ** ****  **
```

Figure 3 (cont)

```
V.salmonicida    NNEYKFNLSKAQRQLMEAWNKQYPVSTWECTRDERIAKIQCNHNQFVYKACTK------- 213
V.cholerae       SEQYGLRLSKAQNQLMQAWNNQYPVSEWECVRDQKIEKVQGNSNRFVREQCPN------- 211
Oceanimonas sp.  QQQYRLKIARQQQKLFEAWNRQYPASPWECERDNRISRIQGNHNPFVQEQCKNYAYIPNP 218
Salmonella sp.   RDQYQLKLSRQQTQLFNVWDKQYPVTAWECERDARIAKVQCNHNPYVQRACQARKS---- 213
Enterobacter sp. RDRYNLNLSRQQTQLFNAWNKQYPVTEWECQRDERIARVQGNHNPYVQRACQAQKS---- 213
Yokenella sp.    RDRYQLALSRQQTQLFNAWDKQYPVSEWECERDERIAKYQGNHNPYVQRACQAQKS---- 213
Klebsiella sp.   RDRYQLNLSRQQTQLFTAWNKQYPVTAWECERDERIAKVQGNHNPYVQQACQAQKS---- 213
E.coli           RDQYNLTLSRQQTQLFNAWNKMYPVTDWECERDERIAKVQGNHNPYVQRACQARKS     213
Shigella sp.     RDQYNLTLSRQQTQLFNAWNKMYPVTDWECERDERIAKVQGNHNPYVQRACQARKS---- 213
Citrobacter sp.  RDQYSLTLSRQQTQLFNAWNKQYPVTDWECERDERIAKVQGNHNPYVQRACQAQKS---- 213
Cronobacter sp.  RDKYQLNLSRAQTQLFEAWNKLYPVTPWECTRDERIAKVQGNHNPYVQQACQGQNR---- 214
Rahnella sp.     RDQYKLNLSRQQTQLFTAWDRQYPVTAWECERDNRIARVQGNHNPYVQQACAQRKS---- 226
Erwinia sp.      RDQYQLSMSKQQTQLMTAWSKLYPVTPWECERDRRIARVQGNHNPYVQQACQR------- 223
Yersinia sp.     RDQYQLRLSSQQSKLFGVWDRQYPVTDWECLRDERIAKTQGNHNPYVQRACQRPKS---- 213
Serratia sp.     RDRYHLRLSRQQTQLFEVWNRQYPVSQWECQREARIAKVQGNRNPYIQQACQRQKG     213
Pseudomonas sp.  SKQYNLRLSRQDQQLYQAWDKTYPPQIWERQRNQQVACVMGRGNEFVGPVDLKACK---- 213
                  *    *   **   *   *     *  *
```

Figure 4

```
                          ↓
V.salmonicida    APPSSFSKAKKEAVKIYLDYPTSFYCGCDIWKNKKKGIPELESCGYQVRKQEKRASRIE 60
V.fischeri       APPSSFSKAKKEAVKIYLDHPTSFYCGCDIWKDKKKGIPDLQSCGYNVRKQEKRASRIE 60
V.wodanis        APPSSFSKAKKLAVKIYLDHPTSFYCGCDIWKDKKKGIPDLESCGYEVRKQEKRASRIE 60
V.splendidus     APPSSFSKAKKEAVKIYLDHPTSFYCGCDIWKDKKKGIPDLDGCGYQVRKQQKRASRIE 60
V.cholerae        APISFSHAKNEAVKIYRDHPVSFYCGCEIRWQGKK GIPDLESCGYQVRKNENRASRIE 58
V.harveyi        APPSFSAAKREAVKIYADHPTSFYCGCDIKWQGKK-GIPDLASCGYQVRKQEKRASRIE 59
V.rotiferianus   APPSSFSAAKREAVKIYADHPTSFYCGCDIKWQGKK GVPDLASCGYQVRKQEKRASRIE 59
V.tubiashii      APPSSFSKAKKEAVKIYADHPTSFYCGCNISWQGRK-GIPDLESCGYQVRKQQKRASRIE 59
V.sinaloensis    APPSSFSKAKKEAIKIYADHPSSFYCCCDIWQCRK-GTPDLNSCCYQVRKEKRASRIE 59
V.vulnificus     APPSSFSAAKQQAVKIYQDHPISFYCGCDIEWQGKK-GIPNLETCGYQVRKQQTRASRIE 59
V.furnissii      -APASFSQAKREAVKIYQDHPVTFYCCCDIQWQCKK-GTPDLKGCCYQVRKQEKRASRIE 58
V.anguillarum    APPASFSQAKKEALKIYHDHPVSFYCGCDIAWQGKK-GTPDLQACGYQVRKQQTRASRIE 59
                   ***  **  *  ***  *  ***** *   *  * * ***  ***  ******

V.salmonicida    WEHVVPAWQFGHQRQCWQKGGRKNCTRNDKQFKSMEADLHNLVPAIGEVNGDRSNFRFSQ 120
V.fischeri       WEHVVPAWQFGHQRQCWQDGGRKNCTRKDKQFKLMEADLHNLVPAIGEVNGDRSNFRFSQ 120
V.wodanis        WEHVVPAWQFGHQRQCWQDGGRKNCTKNDKNFKMMEADLHNLVPAIGEVNGDRSNFRFSQ 120
V.splendidus     WEHVVPAWQFGHQRQCWQDGGRKNCTRNDKVFKSMEADLHNLTPAIGEVNGDRSNYNFSQ 120
V.cholerae       WEHVVPAWQFGHQLQCWQQGGRKNCTRTSPEFNQMEADLHNLTPAIGEVNGNRSNFSFSQ 118
V.harveyi        WEHVVPAWQFGHQRQCWQNGGRKNCTRNDNVFKSMEADLHNLTPAIGEVNGDRSNYNFSQ 119
V.rotiferianus   WEHVVPAWQFGHQRQCWQNGGRKNCTRNDKVFKSMEADLHNLTPAIGEVNGDRSNYNFSQ 119
V.tubiashii      WEHVVPAWQFGHQRQCWQNGGRKNCTKNDKAFRMMEADLHNLTPAIGEVNGDRSNYNFSQ 119
V.sinaloensis    WEHVVPAWQFGHQRQCWQNGGRKNCNDNVFRSMEADLHNLTPAIGEVNGDRSNYNFSQ 119
V.vulnificus     WEHVVPAWQFGHQRQCWQKGGRKNCSKNDQQFRLMEADLHNLTPAIGEVNGDRSNFNFSQ 119
V.furnissii      WEHVVPAWQFGHQLQCWQQGGRKQCSRHDTAFKRMEADLHNLTPAIGEVNGDRSNLNFSQ 118
V.anguillarum    WEHVVPAWQFGHQRQCWQQGGRKNCTKNDTIFRSMEADLHNLTPAIGEVNGDRSNYNFSQ 119
                 ************ **** **** *   *  ******** ******* ***   ***

V.salmonicida    WNGSKGAFYGQCAFKVDFKGRVAEPPAQSRGAIARTYLYMNNEYKFNLSKAQRQLMEAWN 180
V.fischeri       WNGNKGAYYGQCAFKVDFKGRVAEPPAQSRGAIARTYLYMNQEYRFNLSKSQRQLMNAWD 180
V.wodanis        WNGSKGANYCQCAFKVDFKGRVAEPPAQSRGAIARTYMYMNKEYRFNLSKAQRQLMEAWD 180
V.splendidus     WNSMDGVSYGQCEMQVNFKQRKVMPPDRAKGSIARTYLYMSQEYGFKLSKQQTNLMMAWN 180
V.cholerae       WNGIDGVTYGQCEMQVNFKERTAMPPERARGAIARTYLYMSEQYGLRLSKAQNQLMQAWN 178
V.harveyi        WNCMDGVSYCRCEMQVNFKQRKVMPPDRARGSIARTYLYMSKEYCFKLSKQQTQLMSAWN 179
V.rotiferianus   WNGMDGVSYGRCEMQVNFKQRKVMPPDRARGSIARTYLYMSKEYGFKLSKQQTQLMSAWN 179
V.tubiashii      WNGIDGVSYGRCEMQVNFKHRKVMPPDRAKGSIARTYLYMSQEYGFRLSKQQTQLMNAWN 179
V.sinaloensis    WNGVDGVSYGRCEMQVNFKQRKVMPPDRAKGSIARTYLYMSKEYGFKLSKQQTQLMTAWN 179
V.vulnificus     WNGMDGVSYGRCEMQVNFKQRKVMPPDRARGSIARTYLYMSEYGFQLSKQQQQLMQAWN 179
V.furnissii      WHGIDCATYCQCEIQVNFQQRKVMPPERARGAIARTYLYMSQEYGFRLSKSQTQLMQVWN 178
V.anguillarum    WNGVEGESYGRCEMQVDFKQRKVMPPDRARGSIARTYLYMSQNYGFQLSKSQTQLMQAWN 179
                  *   *  ** * *  *   **   * ***** **   *   *** *  **

V.salmonicida    KQYPVSTWECTRDERIAKIQGNHNQFVYKACTK- 213
V.fischeri       KQYPVSEWECERDKRIAKIQGNHNQFVYKACRK- 213
V.wodanis        KQYPVSAWECERDQRIAKIQGNHNQFVFKACTK  213
V.splendidus     KQFPVNEWECTRDERIFAIQGNHNPFVYQACK-  212
V.cholerae       NQYPVSEWECVRDQKIEKVQGNSNRFVREQCPN- 211
V.harveyi        KSYPVDKWECERDERIAKIQGNHNPFVQEACRA  212
V.rotiferianus   KTYPVDKWECERDERIAKIQGNHNPFVQEACRA- 212
V.tubiashii      KQFPVDHWECEREQRIFKVQGNHNPFVHQACQAL 213
V.sinaloensis    KQFPVDEWECERDKRIFKVQCNHNP--------- 204
V.vulnificus     KSYPVDEWECTRDDRIAKIQGNHNPFVQQSCTVR 213
V.furnissii      RQYPVSDWECERDQRIFKVQGNHNPFVRQQCSS  211
V.anguillarum    RQYPADEWECKRDQRIAKVQGNHNPFVQQQCRS- 212
                   **    ***  *    ***  *
```

ENDONUCLEASES

This application is a filing under 35 USC 371 of PCT/GB2013/050387, filed 18 Feb. 2013 which claims priority to GB Application N. 1202768.6, filed 17 Feb. 2012 and GB Application No. 1216029.7, filed 7 Sep. 2012. These prior applications are incorporated herein by reference.

The present invention relates to endonucleases that are inactivated by gentle treatment conditions, in particular showing thermolabile properties. The invention also comprises the removal of contaminating polynucleotides from a biological preparation through the use of such an endonuclease. The invention also relates to the prevention of false positive results in nucleic acid amplification reactions through the use of an endonuclease, in particular amplification reactions which involves a polymerase chain reaction (PCR) set-up.

Nucleic acids, and especially genomic DNA, often poses a problem in cell cultures, cell lysates and protein purification and analysis as it creates viscosity in the sample or interferes with purification, downstream analysis or applications. Removal of DNA and nucleic acid can be done physically, chemically or enzymatically. Enzymatic removal of DNA and RNA can be achieved by adding nucleases. However, nucleases often fail to degrade DNA in complex biological samples, because DNA is bound to proteins or other molecules protecting it from enzymatic degradation. Sodium chloride is often added to typical cell lysis buffers to limit protein-DNA interactions, and thus facilitate the removal of DNA in downstream protein purification. Unfortunately most nucleases become highly inhibited or inactive at moderate salt concentrations, often making enzymatic removal inefficient. Thus, removing all traces of DNA from proteins, reagents or biological samples is often troublesome.

Several commercial alternatives exists to enzymatically remove nucleic acids in cell lysates, protein purification and before analytical steps, such as Benzonase (*Serratia marcescens* nuclease), Omnicleave (Epicentre) or DNaseI. However, there is no option that can be inactivated by moderate heat-treatment. To remove the above enzyme after use, various resins, inhibitors or column purification steps are typically needed. This makes an enzymatic method more troublesome to use since an additional reagent or purification step is needed to remove the nuclease after use. This is more time consuming and may lead to lower yield of the protein of interest.

Problems with removing traces of DNA in protein purification or from reagents are evident in the endogenous DNA often found in commercial polymerases and master mixes. Furthermore, reagents for molecular biology applications (e.g. PCR and sequencing) and molecular diagnostics have to be free of both contaminating DNA and nucleases. The difficulties associated with removing the nucleases described above after use make them less suitable to clean up reagents used for DNA technologies.

Nucleic acid amplification techniques such as PCR's are one of the most powerful tools available in biotechnology, allowing preparation of a large number of copies of a target sequence from a sample containing only a small amount of nucleic acid. In the case of PCR, oligonucleotide primers complementary to their respective strands of a double stranded target sequence are added to the reaction mixture containing the target sequence and free nucleotides. Thermal cycling in the presence of a DNA polymerase results in amplification of the sequence between the primers. The ability of the amplified fragments created by the PCR process to act as templates for subsequent PCR cycles results in the rapid production of a considerable quantity of the target sequence.

Amplification reactions of particular susceptibility to the detrimental effects of nucleic acid contamination are the quantitative PCR (qPCR) techniques, as these have the power to quantify less than 20 copies of a DNA sequence in a reaction. Thus, even the smallest levels of nucleic acid contamination can give false results in qPCR techniques. In addition, these methods require the detection of signals from the amplified target nucleic acids above an inevitable background signal. Contaminating nucleic acid can contribute to this background signal and so reduce the sensitivity of the technique. As such, minimising contaminating nucleic acid maximises the sensitivity of a quantitative PCR experiment. In experiments where small numbers of copies of target nucleic acids are detected, e.g. quantitative PCR-based pathogen diagnostics and pathogen load quantification, it is paramount that sensitivity of the quantitative PCR is maximised and false positives are minimised. In the field of bacteria identification and diagnostics where segments of highly conserved bacterial DNA are targeted (e.g. 16SrRNA or 23SrRNA genes) by qPCR techniques, nucleic acid contamination arising from the DNA polymerase preparation (which are typically obtained from bacteria and bacterial expression systems) is a major problem. Methods to remove bacterial nucleic acid contaminants efficiently from DNA polymerase preparations are therefore needed. Especially sought are methods that can achieve this without having a detrimental impact on downstream amplification reactions and without damaging the polymerase.

It has been suggested that individual PCR reaction mixtures can be treated prior to addition of the target DNA and Taq DNA polymerase using endonucleases that cut internal to the target sequence thus preventing amplification of contaminating DNA (Furrer et al. Nature. Vol. 346 page 324, 1990). This method requires a decontamination time of 30 minutes and in order to inactivate the endonuclease after decontamination the reaction mixture is boiled. Because of this boiling step, it is necessary to add the DNA polymerase after decontamination. Of course, this represents a further risk of the introduction of carry-over into the pre-amplification mixture and decontamination of the DNA polymerase itself is precluded.

Thermolabile endonucleases that breakdown DNA specifically (DNases) have been described. WO 99/007887 discloses a DNase isolated from *Pandalus borealis* that is substantially irreversibly inactivated after 2 minutes at 94° C. This same enzyme is also substantially irreversibly inactivated after 15 minutes at 65° C. However, these temperatures are too high for certain applications and there is also a desire for removal of contaminating RNA and single stranded DNA (ssDNA).

Endonuclease I is a≈25 kDa periplasmic or extracellular, monomeric enzyme known to cleave both RNA and DNA in a sequence independent manner. It is found in many different Proteobacteria and in Fibrobacter. The structure has a mixed alpha/beta topology containing nine beta strands, five short helixes and five long ones. It is able to cleave plasmids and ssDNA. It cleaves at the 3' side of the phosphodiester bond.

Endonucleases that are thermolabile have been described in the art by Alternark et al (FEBS Journal; 2007, 274: 252 to 263). They describe the endonuclease I isolated from the psychrophilic bacterium *Vibrio* salmonicida (VsEndA, SEQ ID NO: 1). This enzyme was found to have an enzymatic activity of less than 20% activity (compared to the optimum activity of this enzyme) at a temperature of 50° C., compared to almost 100% activity under the same conditions found in the endonuclease I isolated from the mesophilic bacterium *Vibrio cholerae* (VcEndA, SEQ ID NO: 3). Moreover, the rate of irreversible unfolding at 70° C. was higher for VsEndA than for VcEndA.

It has been reported that the VsEndA and VcEndA described above are enzymatically more active in solutions of high salinity, due to the mildly halophilic characteristics of the bacteria *V. salmonicida* and *V. cholerae*. Niiranen et al (FEBS Journal; 2008, 275: 1593 to 1605) show that the catalytic constant ($k_{cat}$) peaks at a salt concentration of 0.25 M and 0.5 M for the VcEndA and VsEndA enzymes respectively.

An endonuclease which can be inactivated at mild temperatures and that does not detrimentally affect the activity of the protein, or other molecule of interest in the preparation, would provide a highly effective and efficient method for removing contaminating polynucleotides from a biological preparation. Ideally, this endonuclease would also be able to tolerate preparations containing a high level of salinity, because sodium chloride is often added to preparations in order to limit DNA-protein interactions and produce a purer protein sample after the addition of the endonuclease. However, there is no endonuclease currently available with these properties.

Inactivation of the nuclease which is not reversed by changes in temperature is especially important for preparations that are to be used in further methods that may be performed at room temperature, or include cycles with a room temperature component. Simple thermolability, i.e. unfolding at a lower temperature than existing enzymes, is insufficient. Inactivation under mild conditions, e.g. low temperatures, needs to be combined with a reasonable yield of correctly folded protein on initial synthesis in order to provide a useful enzyme.

The present inventors have surprisingly found that a single point mutation in the amino acid sequence of the VsEndA enzyme, results in an enzyme that remains enzymatically active, even in preparations of high salinity, and yet can be inactivated under mild conditions. The residue whose substitution results in an enzyme with surprising and advantageous properties is a serine residue found in position 44. This serine residue resides immediately N-terminal of a highly conserved pentapeptide motif (Phenylalanine-Tyrosine-Cysteine-Glycine-Cysteine, or Phe-Tyr-Cys-Gly-Cys, or FYCGC). The sequence of wild type (wt) VsEndA is represented by SEQ ID NO: 1 and shown in FIG. 1. The numbering (44) includes an N terminal signal peptide which is cleaved during transport from cytoplasm to periplasm. The signal sequence is not shown in FIGS. 3 and 4 and the numbering in those figures is adjusted accordingly.

From the findings of Alternark et al (Biological Crystallography; 2006, D62, 1387 to 1391) it has been determined that this serine residue forms part of a complex with a buried chloride ion. This serine residue can be found in varying positions depending on the species of bacteria that the endonuclease I enzyme is derived from (for example, the equivalent serine residue in VcEndA is found at position 42, and the equivalent serine residue in the endonuclease I derived from *V. vulnificus* is found at position 41). From studying the sequences of the endonucleases derived from various bacteria of the *Vibrio* genus, it has been found that the amino acid that interacts with the chloride ion at the 40 to 50 sequence position is not always a serine. In the endonuclease derived from *V. furnissii*, for example, the equivalent amino acid is a threonine.

The present inventors have found that the replacement of this serine residue with a negatively charged or another polar residue leads to an enzyme that has the above properties.

Thus, according to the present invention, there is provided an endonuclease I or an enzymatically active fragment thereof, said endonuclease I having the sequence of SEQ ID No. 1 or a sequence which is at least 60% identical thereto, but wherein the amino acid residue which is immediately N-terminal of the FYCGC pentapeptide motif has been substituted with a residue which is either negatively charged or polar, said endonuclease I or enzymatically active fragment thereof being substantially (irreversibly) inactivated when incubated at 30° C. for 15 minutes in the presence of 10 mM dithiothreitol (DTT).

Alternatively, the present invention provides an endonuclease I or an enzymatically active fragment thereof, said endonuclease I having the sequence of SEQ ID No. 1 or a sequence which is at least 60% identical thereto, but wherein the amino acid residue which is immediately N-terminal of the FYCGC pentapeptide motif has been substituted with a residue which is either negatively charged or polar, wherein said endonuclease I or enzymatically active fragment is substantially (irreversibly) inactivated when incubated at 4° C. for 6 hours in the presence of either 10 mM DTT or 10 mM Tris(2-Carboxyethyl) phosphine (TCEP). It is appreciated that appropriate inactivation conditions are a reflection of temperature, time of incubation and a concentration of any added chemical destabilisers. The above conditions provide tests which define the enzymes of the invention and further sets of conditions and complete assay protocols are described in the Examples.

Alternatively viewed, the present invention provides, for the first time, an endonuclease I or an enzymatically active fragment thereof which is substantially (irreversibly) inactivated when incubated at 30° C. for 15 minutes in the presence of 10 mM DTT, or when incubated at 4° C. for 6 hours in the presence of either 10 mM DTT or 10 mM TCEP.

Thus, while the conditions which provide inactivation may vary, the nature of the preferred substitution is the same and thus, alternatively viewed, the invention provides an endonuclease I or an enzymatically active fragment thereof which is at least 70%, preferably at least 80%, 90%, 95% or 98%, identical to SEQ ID No. 1 or 4, but wherein the amino acid residue which is immediately N-terminal of the FYCGC pentapeptide motif has been substituted with a residue which is either negatively charged or polar.

The negatively charged or polar residue may be either genetically coded or non-genetically coded. Preferably the introduced amino acid is negatively charged. Polarity and charge in the context of amino acids and in particular their side chain functional groups are well understood in the art and are typically assessed under normal physiological conditions.

By "substitution" of the amino acid residue which is immediately N-terminal of the FYCGC pentapeptide motif, it is meant that this residue is replaced by a different amino acid, typically genetically encoded, but possibly a non-genetically coded amino acid or amino acid derivative. Preferably the residue, which is typically serine, is replaced by a negatively charged amino acid, such as glutamic acid or aspartic acid, or another polar amino acid, such as threonine, asparagine or glutamine. Alternatively, said amino acid residue is replaced with a non-genetically amino acid that is either negatively charged or polar. Preferred non-genetically coded amino acids are glutamic acid derivatives such as 4-Fluoro-DL-glutamic acid, γ-Carboxy-DL-glutamic acid and D-2-Aminoadipic acid. In the most preferred embodiment, the amino acid residue which is immediately N-terminal of the FYCGC pentapeptide motif is replaced with glutamic acid.

In a preferred embodiment, the endonuclease I or enzymatically fragment of the invention is substantially inactivated when incubated for 30 minutes at 50° C. in the presence of 0.5 mM TCEP and residual activity is assessed in the presence of 0.5 mM TCEP; preferably the endonuclease I or enzymatically active fragment thereof is irreversibly inactivated under these conditions.

In a further aspect, the invention comprises a method of removing contaminating polynucleotides from a sample which comprises use of the endonuclease described above. The method will typically comprise contacting the sample with an endonuclease as defined above.

In a preferred embodiment, the sample is a preparation containing a protein of interest, for example a recombinantly produced protein of interest, e.g. an enzyme. Alternatively the protein of interest may be an analyte or other protein which it is desired to purify from a starting material. The preparation may be or be derived from a cell lysate or tissue sample or body fluid.

The protein of interest may be an antibody or antibody fragment. The protein (e.g. antibody) could be useful in diagnostic or therapeutic methods. Thus, the method above described may be used in order to ensure that the diagnostic or therapeutic protein is free from contaminating polynucleotides so that it may be safe to administer.

The protein of interest may be a DNA binding protein or other protein which associates with nucleic acid in solution. In particular, such proteins for which salt may conveniently be used to separate the protein of interest from the nucleic acid, given the observed ability of the endonuclease of the invention to function in the presence of salt.

The endonuclease of the invention may be particularly effective at salt (for example sodium chloride or potassium chloride) concentrations of 50 mM to 1 M, preferably about 500 mM. Many nucleases are inhibited at the high sodium chloride concentrations typically added to cell lysis and purification buffers and the salt tolerance of the endonucleases of the present invention is a particular advantage. Preferably, the endonucleases of the present invention have an optimum catalytic activity (as assessed herein) at 0.5 M sodium chloride or potassium chloride or an activity at this salt concentration which is no less than 60%, preferably no less than 75% of that exhibited at the optimum salt concentration. The "optimum salt concentration" is the concentration of sodium chloride at which the enzyme has its highest catalytic activity. Alternatively viewed, the endonucleases of the invention have an optimum catalytic activity when the concentration of sodium chloride is 0.35 to 0.65 M, preferably 0.45 to 0.55 M, more preferably around 0.5 M.

In another embodiment, the biological preparation is a reagent solution, e.g. that is used in a polynucleotide analysis technique, such as PCR, DNA/RNA sequencing or microarrays. The reagent solution may comprise or consist of a non-protein component or mixture, such as a PCR master mix or a buffer solution. The endonuclease described above could be used to remove any polynucleotide contamination from the reagent, be deactivated, and then said reagent be applied to a sample containing polynucleotide of interest, thus reducing the likelihood of contamination being introduced to a sample through the addition of said reagent.

The invention has utility in preventing or limiting contamination with polynucleotides and in particular in preventing or reducing false positive results and reducing background (positive No-template controls) due to endogenous polynucleotides in amplification reagents and enzymes.

The endonucleases of the invention are suitable for use in the elimination or reduction of endogenous DNA in amplification reactions. This is because the lower the inactivation temperature of the endonuclease the easier it is to inactivate it during the amplification process and the greater the degree of inactivation that can be achieved at any given temperature used in the inactivation step.

The endonuclease of the invention is thus used to degrade non-target polynucleotides present in the amplification reaction mixture or the individual components thereof, e.g. a polymerase. Thereby, non-specific amplification may be reduced or avoided.

As the endonuclease of the invention can be inactivated at low temperatures, in one preferred embodiment, the endonuclease is used to remove contaminating polynucleotides from a solution containing a protein or reagent of interest, wherein said protein or reagent is itself thermolabile at temperatures above 37° C. (the temperature at which the endonuclease is enzymatically active).

Inactivation of the endonuclease of the invention will typically comprise incubation of the endonuclease with an inactivation additive. The inactivation additive destabilises the endonuclease, i.e. renders it more susceptible to unfolding at a given temperature. Endonuclease I contains a coordinated $Mg^{2+}$ and multiple disulphide bonds and the skilled man will be aware of agents which can target these or other properties of the enzyme to destabilise it.

Because of the coordinated $Mg^{2+}$ ion within the endonuclease, the concentration of $Mg^{2+}$ ions may be of importance in the activity of the endonuclease. For this reason, a concentration of $Mg^{2+}$ or $Mn^{2+}$ ions of between 1 to 20 mM, preferably 5 to 10 mM, may be used in the methods of the invention. A PCR or protein purification buffer typically has a $Mg^{2+}$ ion concentration of 5 mM in the form of magnesium chloride.

The inactivation additive may be a metal ion chelating agent, such as ethylenediaminetetraacetic acid (EDTA). The inactivation additive may also be a disulphide bond reducing agent (i.e. an agent that inhibits and/or disrupts disulphide bonds between two or more cysteine residues in a protein). Examples of such agents include, but are not limited to DTT, 2-mercaptoethanol (also known as β-mercaptoethanol), 2-mercaptoethylamine.HCl, TCEP (Tris(2-Carboxyethyl) phosphine) and N-ethylmaleimide. TCEP and DTT are preferred, TCEP is especially preferred. The skilled man would be able to determine the appropriate concentrations of disulphide bond reducing agent for his needs that would improve inactivation but would not be detrimental to his downstream reactions. For instance, DTT can conveniently be incorporated into the inactivation step at a concentration of between 0.05 and 50 mM.

Preferably, inactivation of the endonuclease in the methods of the invention occurs at a concentration of inactivation additive (e.g. DTT) of between 0.5 and 50 mM, more preferably between 1 and 20 mM, e.g. 5-20 mM.

Thus preferably inactivation additive is present at a concentration of at least 1 mM.

As shown in the Examples, the conditions required for inactivation represent a flexible combination of incubation temperature and time and inactivation additive concentration. Thus, inactivation may be achieved at 40° C. with 1 mM TCEP after 5-10 minutes of incubation, or at 30° C. with 10 mM DTT for 15 minutes. It will be apparent to the skilled man, depending on the nature of the biological preparation to be treated and on the subsequent uses thereof, which combination of conditions is appropriate. The endonucleases of the invention are thermolabile but it should be appreciated from the foregoing that it may not be necessary to heat the enzyme in order to inactivate it.

Thus, in a further aspect, the present invention provides a method of removing nucleic acid (contamination) from a sample which comprises contacting the sample with an endonuclease of the invention under conditions which permit digestion of any polynucleotide therein and then contacting said sample and endonuclease mixture with an inactivation additive at a temperature and for a time sufficient to inactivate said endonuclease.

The two contacting steps will typically be incubations and are described herein, in particular in the Examples. Suitable incubation conditions to achieve digestion of nucleic acids in the sample are known in the art and may conveniently comprise incubation at 10-50° C., e.g. at or around 35-37° C. for 5-30 minutes, e.g. 10-20 minutes, preferably around 15 minutes.

As described elsewhere herein, the incubation conditions for inactivation can vary considerably, at temperatures below 10° C. incubation may be for 1-24 hours, at temperatures from 10-30° C. incubation may be for 10 minutes to 2 hours and at temperatures above 30° C., (for example 30-70° C., more preferably 40° C.), incubation will typically be for 5-30 minutes. As shown in the Examples herein, the concentration and choice of inactivation additive will also affect the incubation times/temperature. Inactivation additives will preferably be used at the aforementioned low incubation temperatures.

Alternatively viewed, this aspect of the invention provides use of the endonuclease of the invention in removing nucleic acid contamination from an amplification reaction mixture or reagent.

In a further aspect the invention also provides a method of preventing or reducing false positive results due to carry-over in nucleic acid amplification reactions, said method comprising using the endonuclease of the invention to degrade carried-over non-target polynucleotides present in the amplification reaction mixture, or the individual components thereof.

The endonuclease of the present invention can also be used to remove nucleic acid contaminants from DNA polymerase preparations as well as being used to remove nucleic acid contaminants from amplification reaction mixtures comprising a DNA polymerase. The low inactivation temperature of the endonuclease of the present invention means that the inactivation of the endonuclease after decontamination can be achieved without a detrimental impact on the polymerase.

The term "nucleic acid amplification reaction" refers to any in vitro means for increasing the number of copies of a target sequence of nucleic acid. Preferably, methods will involve "thermal cycling", i.e. involving high temperature cycling. Amplification methods include, but are not limited to, PCR and modifications thereto, 3SR, SDA, LAR or LCR and LAMP and modifications thereto. PCR, LAMP and LCR and their modifications are thermal cycling methods. Methods may result in a linear or exponential increase in the number of copies of the target sequence. "Modifications" encompass, but are not limited to, real-time amplification, quantitative and semi-quantitative amplification, competitive amplification, and so on.

The target nucleic acid may be DNA or RNA depending on the selected amplification method. For example, for PCR the target is DNA, although when combined with a reverse transcription step the target can be considered to be an RNA sequence. 3SR amplifies RNA target sequences directly.

The term "amplification reaction mixture" refers to any solution, generally aqueous, comprising the various reagents used to amplify a target nucleic acid. These include enzymes, aqueous buffers, salts and nucleoside triphosphates. The term refers to mixtures which contain all the necessary components for carrying out a successful amplification reaction and to mixtures which are incomplete and therefore contain only some (e.g. at least 2, 3 or 4) of the required components. If prefaced by the term "complete" the reaction mixture contains all of the components necessary for amplification.

The term "carry over" is used to describe any nucleic acid which is accidentally or unintentionally introduced into a reaction mixture, in particular target sequences carried over from previous amplification reactions.

The term "false positive result" refers to a result which appears to show that the nucleic acid sample under investigation contains the target sequence but wherein the amplified product is derived from carry-over. Clearly, the reduction in contaminating DNA which the invention provides is particularly advantageous in the forensic and diagnostic fields. The methods of the invention enable the specificity and sensitivity of nucleic acid amplification to be increased.

The term "endonuclease" refers to an enzyme which hydrolyzes a phosphodiester bond in the polynucleotide backbone and is not nucleotide sequence specific. The "endonuclease I" of the present invention can cleave ds and ss polynucleotides, DNA and RNA.

The term "polynucleotide" refers to any chain of nucleotides. These polynucleotides can be RNA or DNA, and can be either double stranded or single stranded. The strands may also be either linear or super-coiled.

The term "salt" refers to any ionic compound that results from the neutralisation reaction of an acid and a base. Salts that are of interest are those that are commonly used to limit DNA-protein interactions and produce a purer protein sample after the addition of an endonuclease, and the skilled person would be aware of these salts. Salts or particular importance are sodium chloride and potassium chloride.

By "substantially inactivated" is meant that the enzyme is at least 95% inactivated, preferably 98% inactivated, more preferably the enzyme is 100% inactivated. Percentage inactivation can be conveniently measured by incubating a DNA sample (e.g. 500 bp PCR product) for 3 hours either with an inactivated endonuclease or with a non-inactivated endonuclease in a suitable buffer (e.g. Tris, HEPES, PBS) at 37° C.; separating the reaction products on an ethidium bromide agarose gel by electrophoresis and measuring the relative intensities of fluorescence of the relevant DNA bands under UV light. Alternative methods could be devised by the skilled man to measure to relative activities of inactivated and non-inactivated endonucleases. For instance, relative changes in fluorescence of SYBR green containing DNA samples could be used. Further methods are the Kunitz assay (Kunitz, M; 1950, S. Gen Physiol, 33:363 and WO 2011/010094) and the modified Kunitz assay devised by Yamamoto (Yamamoto, M; 1971, Biochem Biophys Acta, 228:95 and WO 2011/010094). Suitable methods are described in the Examples herein.

The benefit of "irreversible" inactivation is that the catalytic function of the endonuclease cannot be regained by changes in temperature and therefore the treated sample, which may still contain the inactivated endonuclease, can be used in further processing or applications which involve contact with nucleic acid of interest without digestion of that nucleic acid. Thus, the endonuclease does not regain its activity and there is substantially no residual activity; specifically, less than 5%, preferably less than 2%, most preferably no detectable endonuclease activity remains. The enzymes of the invention are capable of such "irreversible" inactivation (conditions which provide such inactivation are described herein) and thus inactivation is preferably irreversible inactivation. Inactivation can be considered "irreversible" even if it is dependent on the continued presence of an inactivation additive, e.g. a metal ion chelating agent or reducing agent.

Inactivation, including heat change resistant ("irreversible") inactivation, may require the endonuclease to still be in contact with an inactivation additive, as defined above. Unless otherwise clear from the context, residual activities described herein assume the continued presence of an inactivation additive, e.g. at least 0.1, preferably at least 0.2 mM of additive, e.g. TCEP; weaker reducing agents (e.g. DTT) may require higher concentrations, for example at least 0.5 or 1 mM. Typically no more than 10 mM, preferably no more than 5 mM is required or present.

For certain applications, it may be desirable to have an endonuclease I which is inactive even when no, or essentially no, inactivation additive is present. Methods for removal of inactivation agent are known in the art and include dialysis and the use of desalting or buffer exchange columns. The enzymes of the present invention, if treated appropriately, can be inactivated to this extent. Suitable conditions are described in Example 8. Appropriate conditions will depend on (i) the choice of inactivation additive used, (ii) the concentration of inactivation additive added to the endonuclease (iii) the inactivation temperature the endonuclease is heated to (in the presence of inactivation additive) (iv) the time at which the endonuclease is incubated at the inactivation temperature, (v) the temperature the endonuclease is stored at after cooling from the inactivation temperature (in the presence of the inactivation additive) and (vi) the time at which the endonuclease is incubated at the storage temperature.

The skilled man would appreciate that alterations to some of the parameters that favour inactivation, such as an increase in the concentration of the inactivation additive, may affect the other parameters, such as the time the endonuclease needs to be stored at the storage temperature in the presence of the inactivation additive, in order for irreversible inactivation to occur.

By way of example, the inventors have found that VsEndA_S44E may be rendered inactive even in the absence of inactivation agent when 10 mM TCEP is added, the endonuclease is heated to 50° C. for 60 minutes, followed by storage at room temperature for two days (the TCEP is then removed).

Alternatively, if 1 mM TCEP is added to the endonuclease and the endonuclease again heated to 50° C. for 60 minutes but the storage temperature increased to 37° C., the storage time necessary for irreversible inactivation decreases to one day.

It is possible to achieve such inactivation without any initial increase in temperature. For example, for VsEndA_S44E inactivation may be achieved by storing it with 10 mM TCEP for one day at 37° C. or for four days at room temperature. In these cases, the inventors found that even when TCEP was removed by dialysis, the enzyme remained inactive.

The variation of inactivation conditions described above shows the flexibility that the endonucleases of the invention provide. If the sample of interest is known not to be affected by an inactivation additive, the skilled person may choose keep the additive in the sample in order to reduce the inactivation time or temperature. On the other hand, if the skilled person wishes to remove the inactivation additive, he or she may incubate the sample with the inactivation additive for a longer period of time or apply an higher inactivation temperature.

Substantial inactivation preferably occurs within 15 minutes of incubation at a temperature of at or about 30° C., e.g. 28 to 32° C. in the presence of an inactivation additive. The endonuclease of the invention may be substantially inactivated at lower temperatures or over shorter time periods but, in accordance with the invention, heating for about 15 minutes at about 30° C. in the presence of DTT is preferably sufficient to substantially inactivate the enzyme. It will be readily apparent to the skilled man that adjustments to one of these two parameters can be compensated for by adjusting the other. For instance increasing the inactivation temperature might permit the duration of incubation to be reduced. Conversely, increasing the duration of incubation might permit a lower inactivation temperature to be used. Of course, as is also readily apparent to the skilled man and shown in the Examples, when the endonuclease of the invention is used in the methods of the invention, durations of incubation longer than 15 minutes may be used and inactivation temperatures greater than about 30° C. may be used.

Inactivation temperatures and times for an endonuclease should be assessed by incubating the endonuclease in a solution that mimics a typical PCR or protein purification buffer (e.g. 25 mM Tris/HCl, pH 8.5, 5 mM $MgCl_2$). The endonuclease should be present at about between 0.1 U/µl and 100 U/µl, preferably between 1 and 50 U/µl, e.g. 25-30 U/µl. Suitable protocols are described in the Examples.

The reaction mixture is preferably at a pH that the sample or protein of interest is stable at. A pH of between 7.0 and 9.5, preferably around 8.5, is particularly suitable with regard to the enzymatic activity of the endonuclease of the invention. A pH of 8.5 would also suit a typical PCR or protein purification buffer.

Advantageously, the thermolabile endonuclease of the invention is fully functional in a complete amplification reaction mixture, and is compatible with standard in vitro amplification reactants and conditions. The enzyme should also be capable of removing suitable amounts of contaminating polynucleotides and/or carry-over from a reaction mixture, usually fg- or pg-levels but preferably up to 1 ng. Preferably, the endonuclease is able to degrade all the carry-over within 60 minutes at 37° C., more preferably within 30 minutes, most preferably within 15 minutes.

Also included within the scope of the present invention are enzymatically active fragments of the endonucleases of the invention, it being appreciated that catalytic activity can be retained in truncated and other variants. The Examples provide a suitable assay of endonuclease activity.

The present invention is exemplified by the preferred S44E mutation to VsEndA and more generally, modified versions of VsEndA are preferred embodiments of endonucleases of the present invention. The serine may be replaced by residues other than Glu(E), in particular by non-genetically coded homologues of Glu or by threonine, asparagine or glutamine. The residue equivalent to serine 44 in other endonuclease I sequences may be substituted. The residue equivalent to serine 44 in VsEndA is shown for other species in the sequence alignments of FIGS. 3 and 4. The following tables show the percentage sequence identity of various *Vibrio* species (Table 1) and a selection of other bacteria (Table 2) with SEQ ID No. 1 (VsEndA). The endonucleases in these tables and the corresponding figures are preferred endonucleases for modification according to the teaching of the present invention and the resulting enzymes are preferred endonucleases of the invention.

TABLE 1

| Sequence 1 | Sequence 2 | % Identity |
|---|---|---|
| V. salmonicida | V. fischeri | 91 |
| V. salmonicida | V. wodanis | 91 |
| V. salmonicida | V. splendidus | 78 |
| V. salmonicida | V. cholerae | 71 |
| V. salmonicida | V. harveyi | 77 |
| V. salmonicida | V. rotiferianus | 77 |
| V. salmonicida | V. tubiashii | 73 |
| V. salmonicida | V. sinaloensis | 74 |
| V. salmonicida | V. vulnificus | 74 |
| V. salmonicida | V. furnissii | 70 |
| V. salmonicida | V. anguillarum | 71 |

TABLE 2

| Sequence 1 | Sequence 2 | % Identity |
|---|---|---|
| V. salmonicida | V. cholerae | 71 |
| V. salmonicida | Oceanimonas sp. | 64 |
| V. salmonicida | Salmonella sp. | 65 |
| V. salmonicida | Enterobacter sp. | 65 |
| V. salmonicida | Yokenella sp. | 66 |
| V. salmonicida | Klebsiella sp. | 65 |
| V. salmonicida | Escherichia coli | 65 |
| V. salmonicida | Shigella sp. | 64 |
| V. salmonicida | Citrobacter sp. | 66 |
| V. salmonicida | Cronobacter sp. | 68 |
| V. salmonicida | Rahnella sp. | 63 |
| V. salmonicida | Erwinia sp. | 62 |
| V. salmonicida | Yersinia sp. | 63 |
| V. salmonicida | Serratia sp. | 62 |
| V. salmonicida | Pseudomonas sp. | 51 |

Preferably the endonuclease of the invention is a *Vibrio* endonuclease or derived therefrom. A further particularly preferred modified endonuclease according to the present invention is from *Vibrio cholerae* (VcEndA), e.g. in which the serine adjacent to the pentapeptide motif is replaced by glutamic acid.

Preferred endonucleases are those which lack the N terminal signal peptide, i.e. are represented by SEQ ID No. 4 or sequences which are at least 60%, preferably at least 70%, 80%, 90%, 95% or 98% identical to SEQ ID No. 4. As the mature endonuclease of the invention lacks the signal peptide, unless otherwise clear from the context, any reference herein to SEQ ID No. 1 can be considered also a reference to SEQ ID No. 4. SEQ ID No. 4 is the first sequence recited in both FIGS. 3 and 4.

Preferred endonucleases of the invention have the sequence of SEQ ID Nos. 1, 3, 4 or 5 but wherein the amino acid residue which is immediately N-terminal of the FYCGC pentapeptide motif has been substituted with a residue which is either negatively charged or polar, preferably negatively charged. Endonucleases of SEQ ID Nos. 1 or 4 in which the serine at position 44 has been replaced with glutamic acid are most preferred.

Further preferred endonucleases of the invention have a sequence of an endonuclease I obtainable from a *Vibrio* species but wherein the amino acid residue which is immediately N-terminal of the FYCGC pentapeptide motif has been substituted with a residue which is either negatively charged or polar, preferably negatively charged.

As discussed herein, the amino acid replacing the residue N terminal of the identified pentapeptide motif should not be hydrophobic. The modified enzyme VsEndA_S44A (alanine) was prepared but the yield was only about 5% of that achieved with S44E and it was highly unstable, quickly losing all catalytic activity.

Percentage sequence identity according to the invention can be calculated using any of the widely available algorithms (e.g. using the Clustal W2 multiple sequence alignment program (www.ebi.ac.uk/Tools/clustalW2) using default parameters (DNA Gap Open Penalty=15.0; DNA Gap Extension Penalty=6.66; DNA Matrix=Identity; Protein Gap Open Penalty=10.0; Protein Gap Extension Penalty=0.2; Protein matrix=Gonnet; Protein/DNA ENDGAP=−1; Protein/DNA GAPDIST=4)

The exact position of the amino acid residue which is immediately N-terminal of the FYCGC pentapeptide motif (i.e. the polar residue that forms part of the complex with the chloride ion) in the endonucleases can be readily identified by using standard sequence alignment techniques such as Clustal W2 to produce alignments such as that represented in FIGS. 3 and 4. If a sequence lacks a fully conserved FYCGC motif it will still be possible using these techniques of sequence alignment to identify the residue equivalent to serine 44 in SEQ ID NO 1.

Nucleic acid molecules encoding the endonucleases of the invention and fragments thereof constitute a further aspect of the present invention, with SEQ ID NO:2 and sequences at least 80 or 90% identical thereto being preferred.

The invention also provides the use of the particular endonuclease described above as a decontaminating agent in methods of amplifying a nucleic acid. The use of the particular endonucleases described above in the decontamination methods described herein represents a particularly preferred embodiment of the invention.

A method for the isolation and purification of an endonuclease or an enzymatically active fragment thereof as described above represents a further aspect of the present invention. Thus, in this aspect the invention provides such a method, said method comprising expressing said endonuclease or fragment thereof in a suitable host cell (e.g. *Pichia pastoris; Escherichia coli; S. cereviciae*, baculovirus infected insect cells), and subsequently separating the endonuclease from said host cells and/or the media in which said cells have been cultured. Expression of said endonuclease or fragment thereof can be achieved by incorporating into a suitable host cell an expression vector encoding said endonuclease or fragment thereof. Host cells comprising these expression cassettes and nucleic acid molecules are encompassed by the invention.

The endonuclease enzyme may be separated, or isolated, from the host cells/culture media using any of the purification techniques for protein known in the art and widely described in the literature or any combination thereof. Such techniques may include for example, precipitation, ultrafiltration, dialysis, various chromatographic techniques, e.g. gel filtration, ion-exchange chromatography, affinity chromatography, electrophoresis, centrifugation etc.

Likewise an extract of host cells may also be prepared using techniques well known in the art, e.g. homogenisation, freeze-thawing etc and from this extract the endonucleases of the invention can be purified.

It has been found that a purification protocol based on a combination of ion exchange chromatography and affinity chromatography, e.g. on a sepharose column, e.g. a Red sepharose (Pharmacia Biotech, Sweden) or a Blue sepharose (GE Healthcare) column, may readily be used to isolate the enzyme.

More particularly, the extract may be subjected to ion-exchange chromatography and the protein eluted with a NaCl gradient. The fractions containing endonuclease activity may be dialysed and then applied to an affinity column before final elution with NaCl.

The yields of the endonucleases of the invention are exceptionally good and thus, alternatively viewed, the invention provides a method of increasing the yield of a recombinantly expressed endonuclease I which comprises substituting the residue immediately N-terminal of the pentapeptide motif FYCGC with a residue which is either negatively charged or polar. Suitable endonucleases which may be modified in this way are described herein and exemplified e.g. in FIGS. 3 and 4. Suitable expression methods are described above.

The present invention also provides kits which comprise at least an endonuclease according to the invention. The kits may also contain some or all of the necessary reagents, buffers, enzymes etc. to carry out nucleic acid amplification reactions. More particularly, the kits may contain nucleotide triphosphates (including dATP containing an α thiol group (dATPαS) for strand displacement Amplification), oligonucleotide primers, preferably those capable of functioning at about 30° C., DNA polymerases, preferably a thermostable polymerase such as Taq polymerase or Bst polymerase (and hot-start versions thereof) or, in the case of LAR, a DNA ligase (preferably a thermostable DNA ligase such as Ampligase® or that disclosed in U.S. Pat. No. 6280998 which is isolated from *Pyrococcus furiosus*) or a restriction enzyme (preferably a thermostable restriction enzyme such as BsoB1). The endonuclease may be provided in one compartment together with a reverse transcriptase, DNA polymerase, strand displacement polymerase or LCR ligase.

Kits may contain written materials as guidance on how to perform procedures related to the invention. In particular guidance on inactivation conditions may be provided. Suitable conditions are described elsewhere herein but, by way of further general examples, which may also be provided with the kit or enzyme, Table 3 gives suggested incubation conditions in the presence of inactivation additive that are suitable for the inactivation of endonuclease derived from *Vibrio salmonicida* with the Ser44Glu mutation (VsEndA_S44E).

TABLE 3

| Temperature (° C.) | Concentration of Dithiothreitol (DTT)/Time | Concentration of Tris(2-Carboxyethyl)phosphine (TCEP)/Time |
| --- | --- | --- |
| 25 | 20 mM/60 min | 15 mM/60 min |
| 40 | 10 mM/30 min | 5 mM/30 min |
| 50 | 1 mM/30 min or 10 mM/15 min | 0.5 mM/30 min |
| 60 | 1 mM/30 min | 0.5 mM/30 min or 10 mM/15 min |
| 65 | 1 mM/30 min | 1 mM/30 min |
| 70 | 1 mM/30 min | 1 mM/30 min |

The present invention also provides compositions comprising an endonuclease of the invention and one or more of the necessary reagents to carry out nucleic acid amplification and methods, e.g. those components described above. Typically such compositions will be aqueous and buffered with a standard buffer such as Tris, HEPES, etc.

In a further aspect, the present invention provides a composition comprising an endonuclease I or active fragment as defined herein together with a second endonuclease I or enzymatically active fragment thereof. Preferably the second endonuclease I or enzymatically active fragment thereof has the sequence of SEQ ID No. 5 or a sequence which is at least 80% identical thereto. The second enzyme may incorporate mutations, e.g. to the native *Vibrio cholerae* sequence which render it more readily inactivated. Such combinations allow the composition as a whole to provide effective endonuclease activity at a greater range of pH and/or salt concentration and/or temperature.

The invention will now be described by way of non-limiting Examples with reference to the following figures in which:

FIG. 1 shows the alignment of the amino acid sequences (including the signal peptide) of the endonucleases derived from *Vibrio salmonicida* (VsEndA) and *V. cholerae* EndA (VcEndA), SEQ ID NO:1 and SEQ ID NO:3 respectively.

FIG. 2 shows the nucleic acid sequence and the amino acid sequence (including the signal peptide) of VsEndA with the Ser44Glu mutation (VsEndA_S44E), SEQ ID NO:2 and SEQ ID NO:6 respectively.

FIG. 3 shows the sequence alignment data of the amino acid sequences (excluding the signal peptides) of wild type endonuclease I derived from bacteria from a variety of different genera.

FIG. 4 shows the sequence alignment data of the amino acid sequences (excluding the signal peptides) of wild type endonuclease I derived from various bacteria of the *Vibrio* genus.

FIG. 8 shows the photographs of agarose gels which show the activity of the endonuclease of VsEndA_S44E and the wild type VsEndA which have been inactivated in the presence of DTT at a concentration of either 1 mM, 10 mM or 20 mM for 15, 30 or 60 minutes at a temperature of either 50° C. (FIG. 8a), 40° C. (FIG. 8b), 30° C. (FIG. 8c) or 25° C. (FIG. 8d). Results were compared against either no enzyme (negative control) or 6 U wild-type VsEndA (positive control).

Figure 9A:
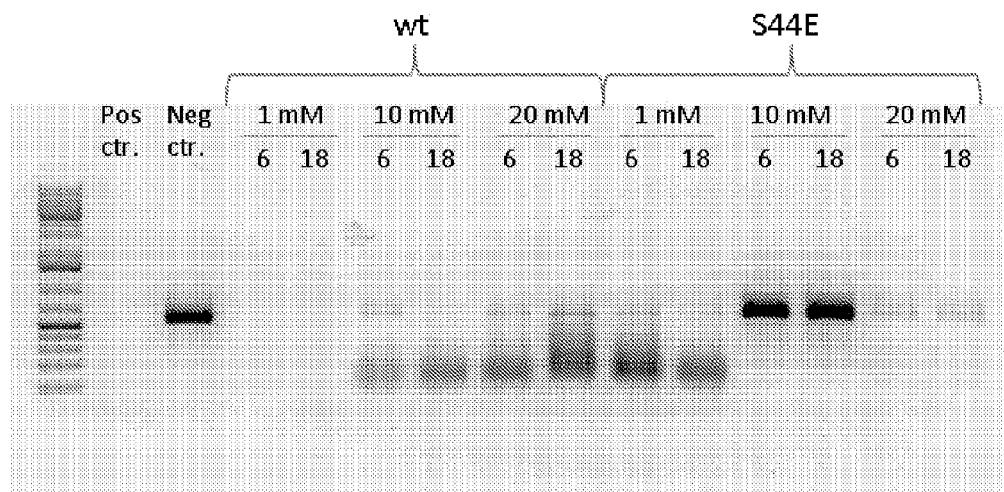
Figure 9B:
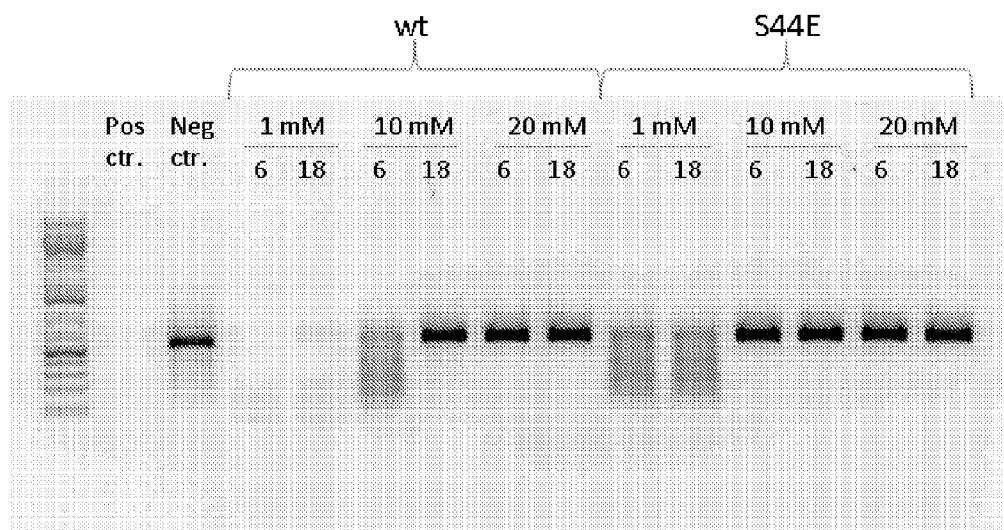

FIG. 9 shows the photographs of agarose gels which show the activity of the endonuclease of VsEndA_S44E and the wild type VsEndA which have been incubated at 4° C. for either 6 or 18 hours in the presence of either DTT (FIG. 9a) or TCEP (FIG. 9b) at a concentration of either 1 mM, 10 mM or 20 mM. Results were compared against either no enzyme (negative control) or 6 U wild-type VsEndA (positive control).

Figure 10A:
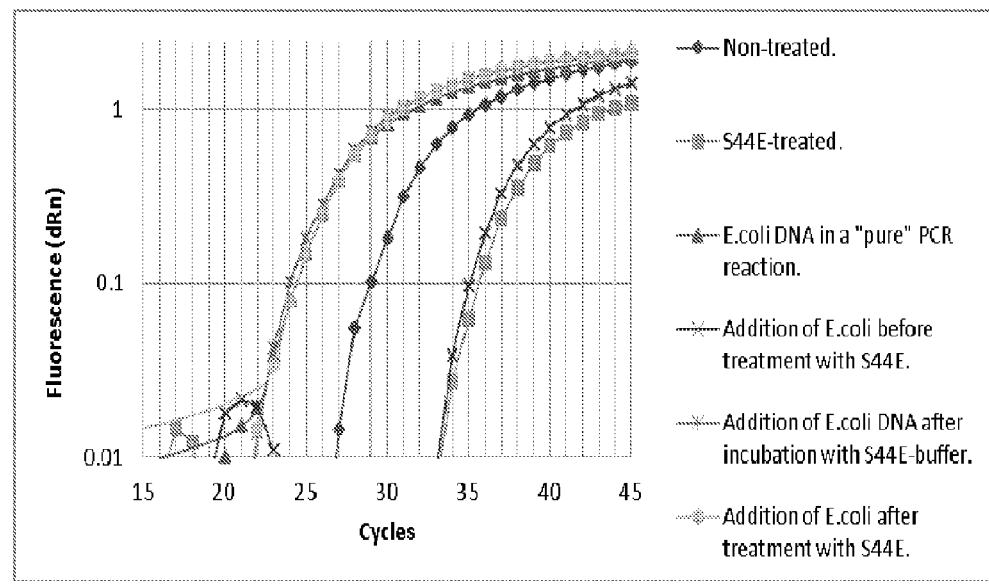
Figure 10B:
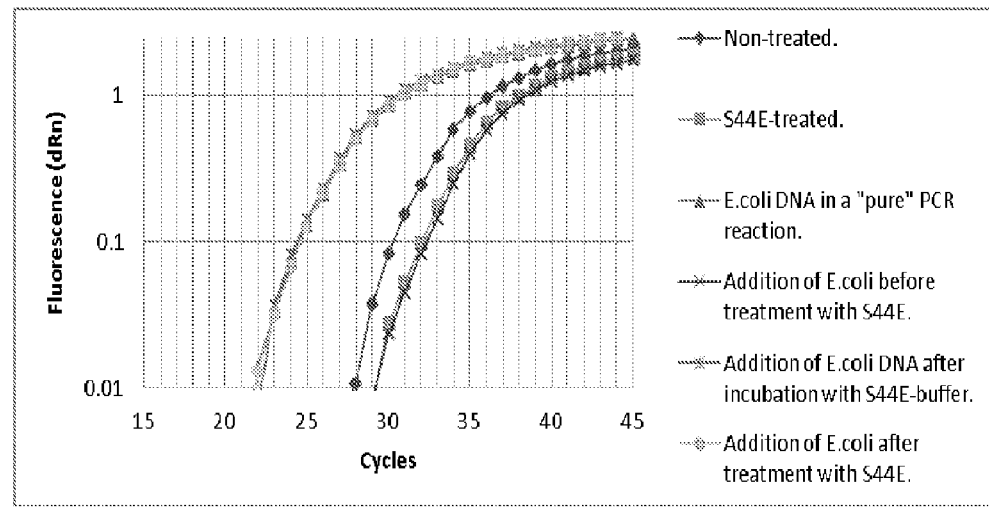

FIG. 10 shows the degree of removal of spiked DNA from the commercially available AccuStart™ Taq DNA polymerase (FIG. 9a) or GoTaq® Hot Start polymerase (FIG. 9b) using the VsEndA_S44E mutant.

Figure 11:
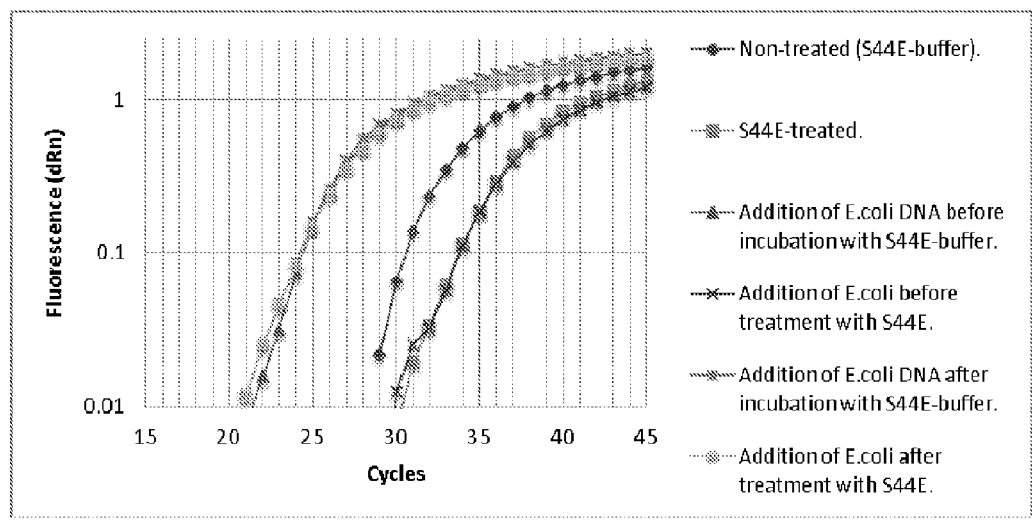

FIG. 11 shows the degree of removal of spiked DNA from commercially available Maxima qPCR master mix using the VsEndA_S44E mutant.

Figure 12A:
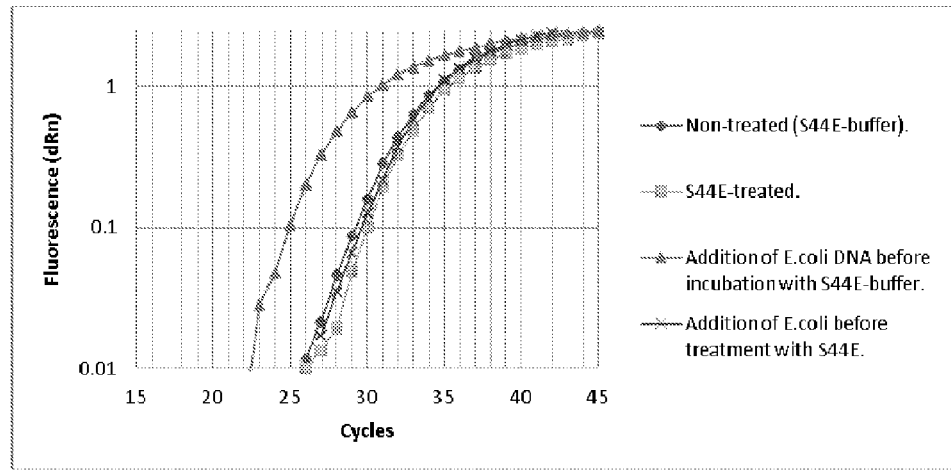
Figure 12B:
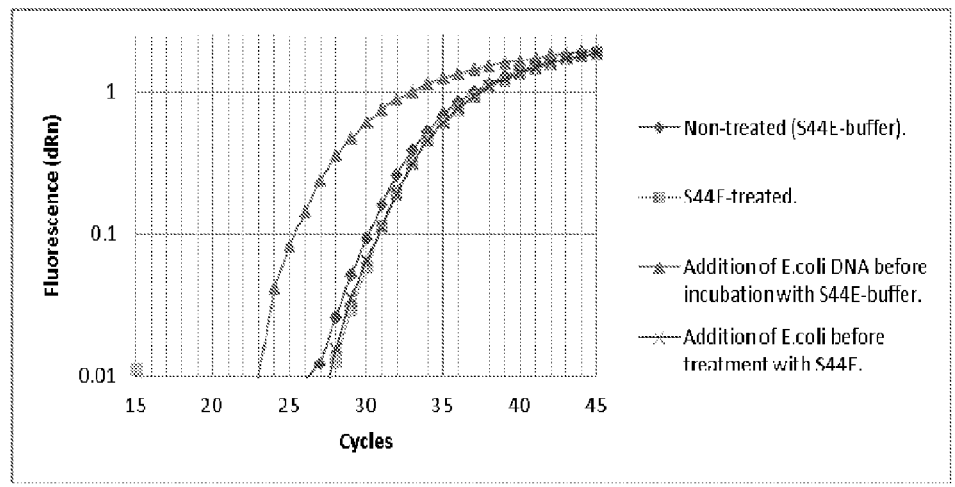

FIG. 12 shows the degree of removal of spiked bacterial genomic DNA from commercially available TEMPase DNA polymerase using the VsEndA_S44E mutant in a solution containing either 0.5 M sodium chloride (FIG. 11a) or 1M sodium chloride (FIG. 11b).

Figure 13:
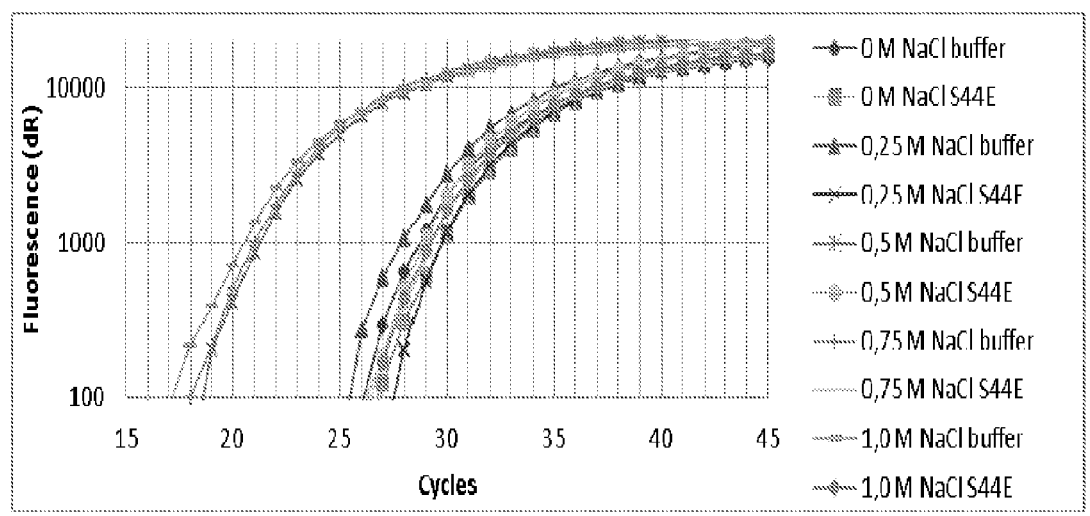

FIG. 13 shows the degree of removal of spiked bacterial genomic DNA from an *E. coli* cell lysate solution containing a recombinantly expressed protein using the VsEndA_S44E mutant in varying sodium chloride solutions (0 M, 0.25 M, 0.5 M, 0.75 M and 1.0 M).

Figure 14:
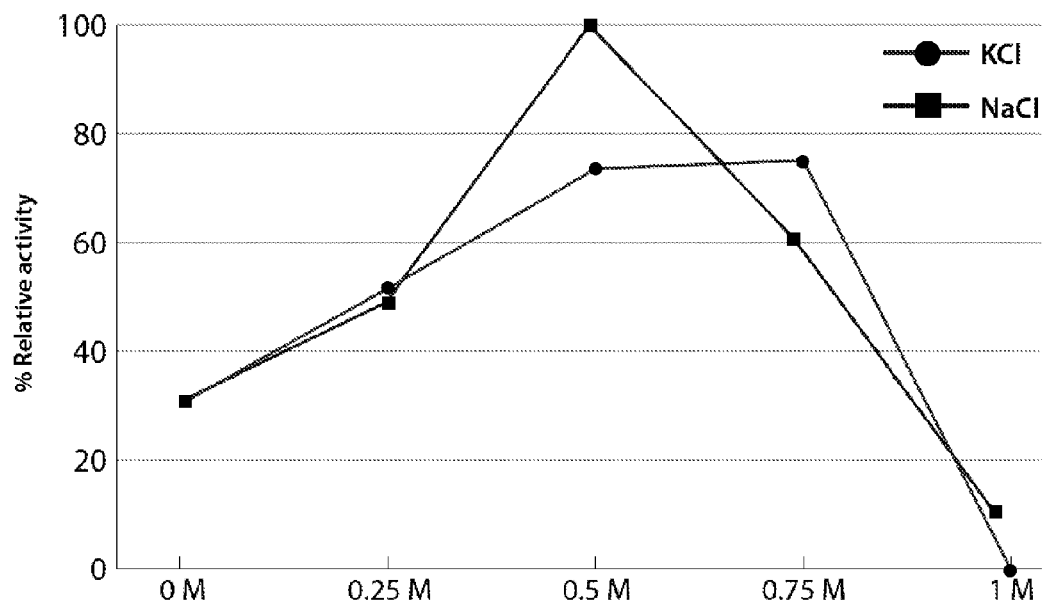

FIG. 14 shows the optimum activity of the VsEndA_S44E mutant in solutions with high salinity. The activity was tested in a 25 mM Tris-HCl buffer, pH 8.5, 5 mM magnesium chloride, with varying concentrations of sodium chloride and potassium chloride. The maximum activity obtained was set to 100%.

Figure 15:
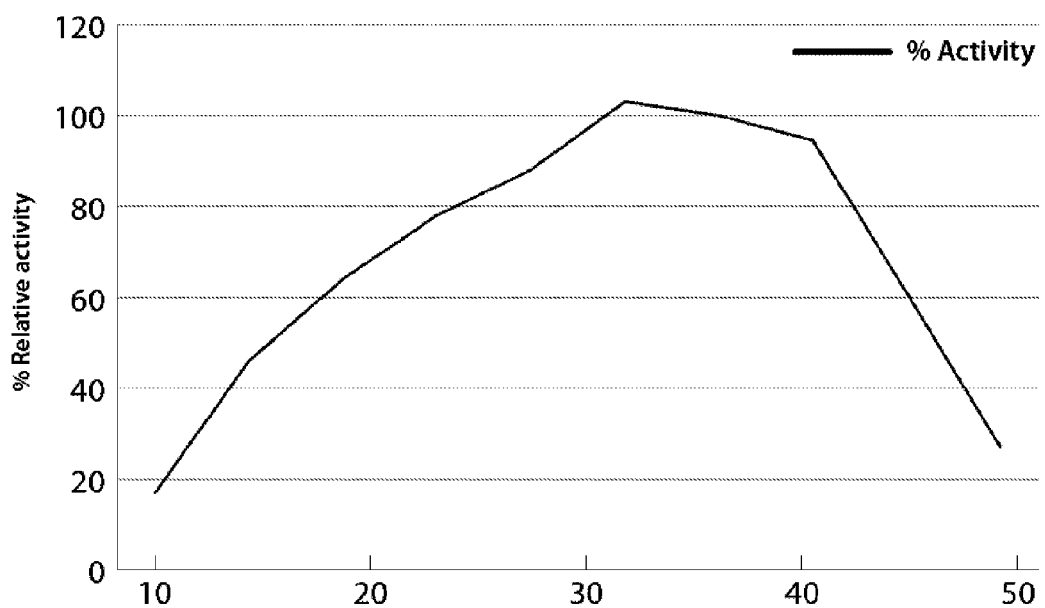

FIG. 15 shows the activity of the VsEndA_S44E mutant at varying temperatures. The activity was tested in a 25 mM Tris-HCl buffer, pH 8.5 containing 5 mM magnesium chloride and 0.5 M sodium chloride.

Figure 16A:
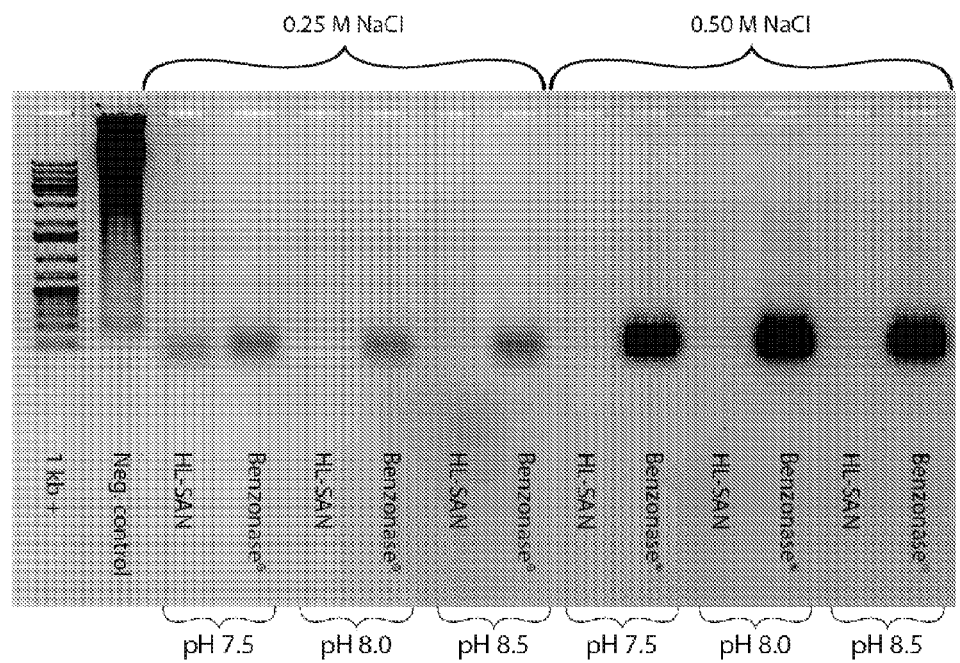
Figure 16B:
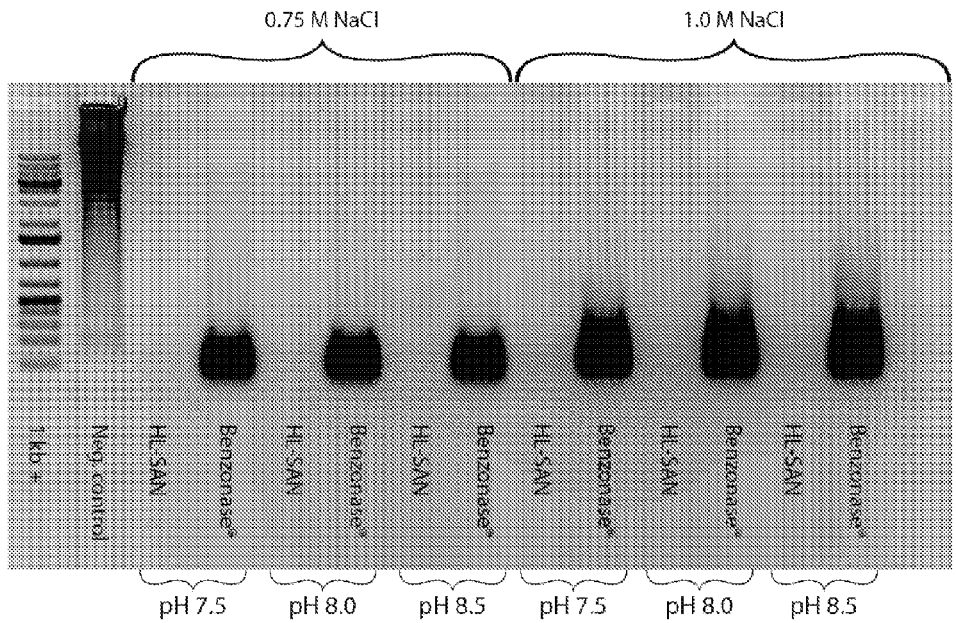

FIG. 16 shows the ability of the VsEndA_S44E mutant to degrade DNA at varying levels of pH and sodium chloride concentrations, as compared to commercially available Benzonase (Serratia marcescens) nuclease. Reactions were carried out at a pH of either 7.5, 8.0 or 8.5 and at a sodium chloride concentration of either 0.25 M or 0.5 M (FIG. 16a) or 0.75 M or 1.0 M (FIG. 16b). Reaction mixtures contained 100 µL Tris-HCl buffer with 5 mM magnesium chloride, 50 µg calf thymus DNA and 300 U of either VsEndA_S44E or Benzonase. Reaction mixtures were incubated at 37° C. for 30 minutes. The reactions were stopped using an EDTA-containing loading buffer and run on a 1% agarose gel.

Figure 17:
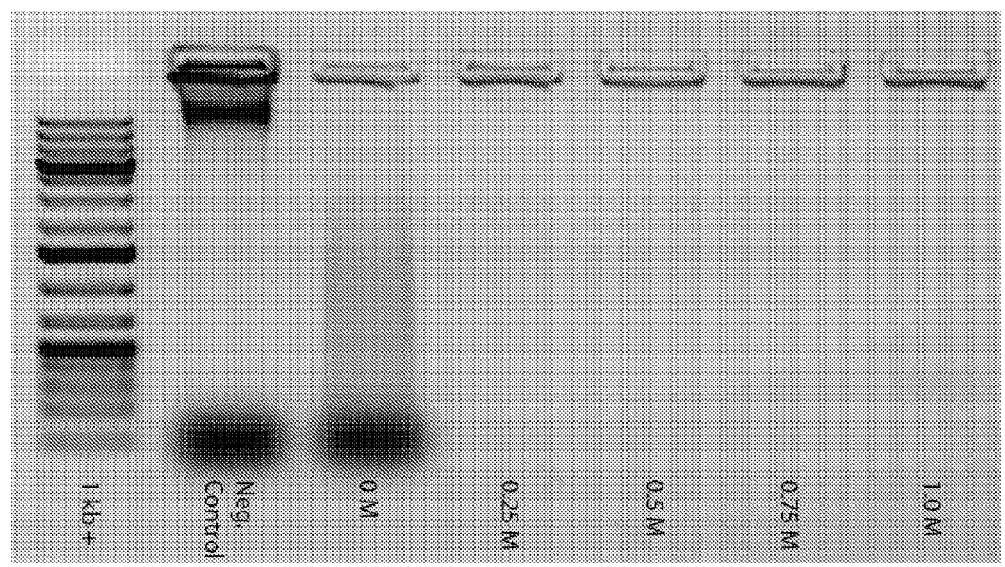

FIG. 17 shows the ability of the VsEndA_S44E mutant to degrade DNA in E. coli lysates containing a DNA binding protein. VsEndA_S44E was added to E. coil lysates at varying sodium chloride concentrations and incubated at 37° C. for 30 minutes. Control contains no sodium chloride.

and in which

SEQ ID NO: 1 is the amino acid sequence of the translated portion of the cDNA nucleotide sequence of the wild-type Vibrio salmonicida endonuclease I, including the signal peptide.

SEQ ID NO: 2 is the cDNA nucleotide sequence of the mutant Vibrio salmonicida endonuclease I (VsEndA with the TCC to GAG mutation) including the signal sequence.

SEQ ID NO: 3 is the amino acid sequence of the translated portion of the cDNA nucleotide sequence of the wild-type Vibrio cholera endonuclease I, including the signal peptide.

SEQ ID NO: 4 is the amino acid sequence of the translated portion of the cDNA nucleotide sequence of the wild-type Vibrio salmonicida endonuclease I, without the signal peptide.

SEQ ID NO: 5 is the amino acid sequence of the translated portion of the cDNA nucleotide sequence of the wild-type Vibrio cholera endonuclease I, without the signal peptide.

SEQ ID NO: 6 is the amino acid sequence of the mutant Vibrio salmonicida endonuclease I (VsEndA, with a serine residue substituted for a glutamic and residue at position 44), including the signal sequence.

SEQ ID NO: 7 to SEQ ID NO: 20 are endonuclease I amino acid sequences, without signal peptide, derived from bacteria from a variety of different genera as described in Table 2 and FIG. 3.

SEQ ID NO: 21 to SEQ ID NO; 30 are endonuclease I amino acid sequences, without signal peptide, derived from various bacteria of the Vibrio genus as described in Table 1 and FIG. 4.

EXAMPLES

Example 1

Cloning and Mutagenesis

The gene for Vibrio salmonicida endonuclease I was PCR amplified from a vector containing the gene and cloned into the pPIC9K expression vector for Pichia pastoris. The native signal sequence of V. salmonicida endonuclease I was omitted in the expression vector, such that the amino acid sequence of V. salmonicida endonuclease I following the α-mating factor encoded by the expression plasmid was APPSSF.

The V. salmonicida endonuclease I (VsEndA) was mutated at residue 44 from serine (Ser) to glutamic acid (Glu) using the QuikChange™ mutagenesis kit from Agilent following instructions from the manufacturer. The pPIC9K vector containing the truncated VsEndA sequence was used as a template. Correct sequence after mutagenesis reactions was verified by DNA-sequencing.

Example 2

Expression and Purification

The pPIC9K-VsEndA_S44E vector was linearized using SacI and transformed into Pichia pastoris GS115 as described in the manual for the Pichia pastoris expression Kit (Life Technologies). The V. salmonicida S44E_endonuclease I (VsEndA_S44E) was expressed in shake flasks essentially as described in the Pichia expression kit. A 50 ml preculture of the GS115 strain containing the VsEndA_S44E in BMGY medium was cultivated overnight at 30° C. The cells were centrifuged and resuspended in 250 ml BMMY and expression was done for 72 h at 20° C. Addition of methanol to a final concentration of 0.5% was done every 24 h. The cells were removed by centrifugation and the supernatant was used as a starting material for purification. The VsEndA_S44E was purified using cationic exchange chromatography. The supernatant (250 ml) was applied on a SP-Sepharose FF (1.6/3) column equilibrated in 25 mM Tris/HCl, pH 8.3, 5 mM MgCl$_2$ using a flow of 5 cm/min. The column was washed with 250 ml of 0.4 M NaCl in the above buffer. Elution of the VsEndA_S44E was done using 25 mM Tris/HCl, pH 8.3, 5 mM MgCl$_2$+1M NaCl. Fractions containing VsEndA_S44E activity were pooled and finally concentrated.

Example 3

Measurement of Nuclease Activity

Nuclease activity may be assayed according to the procedure of Kunitz (Kunitz, M., 1950, Crystalline Deoxyribonuclease, II, Digestion of Thymus Nucleic Acid. The Kinetics of Reaction. J. Gen. Physiol., 33, 363-377). A modified composition of this has been used to measure nuclease activity. Ten µl of enzyme preparation is added to 50 µg calf thymus DNA in 25 mM Tris/HCl, pH 8.5, 0.5 M NaCl, 5 mM MgCl$_2$, in a final volume of 1 ml. The mixture is incubated at 37° C. and increase in absorption is measured at 260 nm. 1 U=0.01 OD$_{260}$ increase×min$^{-1}$.

A study was carried out whereby the activity of the VsEndA_S44E mutant was assessed at various temperature (with no reducing agent present). FIG. 15 shows that VsEndA_S44E has optimum activity at about 35° C., but works over a broad temperature range (20% activity at 10° C. and 50° C.).

Example 4

Comparison of Expression Level of VsEndA_S44E v Wild-Type (VsEndA)

A 50 ml preculture of the GS115 strain containing the pPIC9K-VsEndA_S44E expression cassette was compared to a strain containing the wild type expression cassette. The two strains were cultivated overnight at 30° C. in BGMY medium. The cells were centrifuged and resuspended in 250 ml BMMY and expression was done for 72 h at 20° C. Addition of methanol to a final concentration of 0.5% was done each 24 h and nuclease activity was measured as described.

Figure 5:
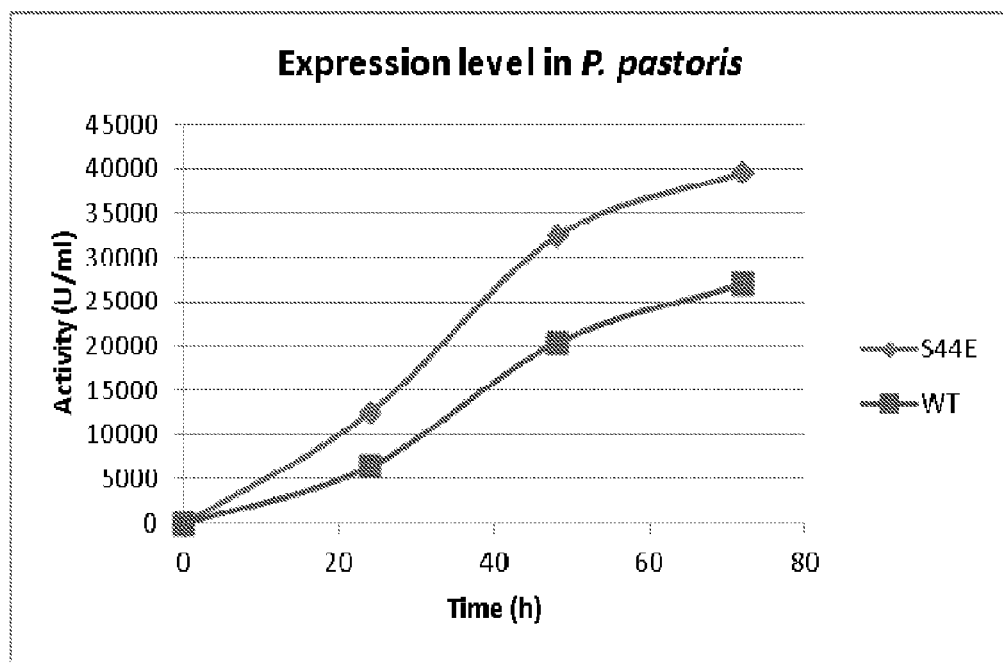
FIG. 5 shows the expression levels of the VsEndA_S44E mutant (the VsEndA endonuclease with the Ser44Glu mutation) and the wild type VsEndA enzyme (SEQ ID NO: 1) in *Pichia pastoris* host cells containing the pPIC9K-VsEndA_S44E and the wild-type expression cassettes respectively.

FIG. 5 shows that the VsEndA_S44E mutant gives a higher expression level in Pichia pastoris than the wild-type VsEndA enzyme in terms of active expressed enzyme measured in U/ml in the cell-supernatant. The VsEndA_S44E mutant has been shortened to "S44E" and the wild-type VsEndA to "wt" in the Figure legends.

After purification as described above (in Example 2), the specific activity of VsEndA_S44E is determined to be about 20% higher than the VsEndA, as shown in Table 4.

TABLE 4

| Endonuclease | Activity (U/ml) | Protein concentration (mg/ml) | Specific activity (U/mg) |
|---|---|---|---|
| VsEndA_S44E | $1.69 \times 10^7$ | 0.69 | $2.4 \times 10^7$ |
| VsEndA | $1.12 \times 10^7$ | 0.56 | $2.0 \times 10^7$ |

Example 5

Temperature Stability of VsEndA_S44E Compared to VsEndA

The half-life of the wild-type (VsEndA) enzyme is approximately 2 h at 70° C. and 5 h at 60° C. (data not shown).

Enzymes, VsEndA_S44E and VsEndA, were diluted to a concentration of 200,000 U/ml in a buffer containing 25 mM Tris/HCl, pH 8, 5 mM MgCl$_2$, 150 mM NaCl, 0.01° A) Triton X-100, and ±1 mM dithiothreitol (DTT). A volume of 6×100 µl was transferred to different eppendorf tubes. The samples were incubated at 40° C. or 50° C. for 0 to 40 minutes and thereafter placed on ice sequentially. The remaining activity was measured using the modified Kunitz assay as described in Example 3. From the data shown in FIG. 6, it is evident that for both VsEndA_S44E and VsEndA, the addition of DTT is required for heat-inactivation. Upon addition of DTT the enzymes inactivate at a faster rate. The VsEndA_S44E mutant has been shortened to "S44E" and the wild-type VsEndA to "wt" in the Figure legends.

Example 6

Temperature Inactivation Using Different Reducing Agents

The ability of VsEndA_S44E to be inactivated using a range of inactivation additives comprising DTT, Tris(2-Carboxyethyl) phosphine (TCEP) and 2-mercaptoethanol was tested at a temperature of 40° C.

Figure 6A:
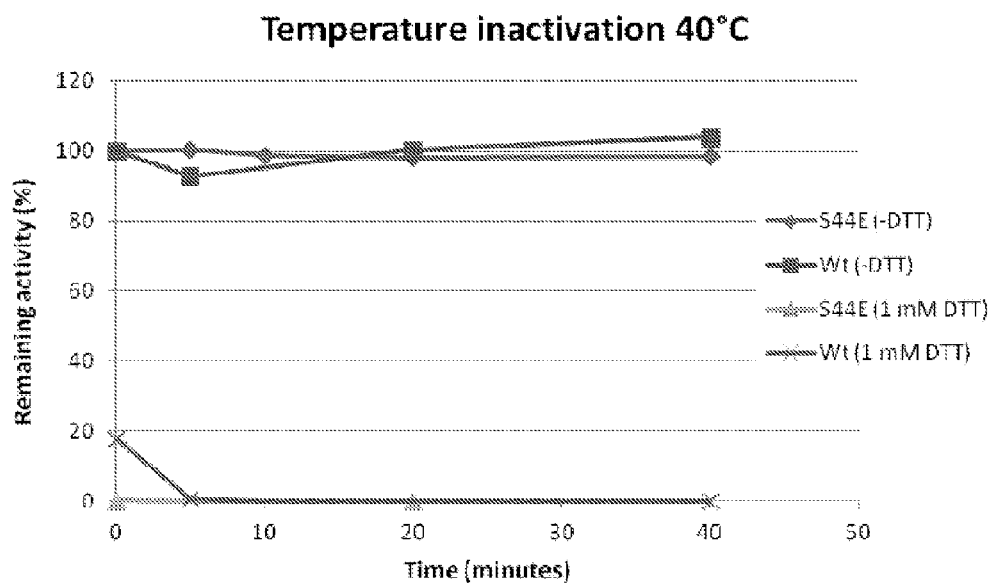
FIG. 6 shows the rate of VsEndA and VsEndA_S44E inactivation at 40° C. (6a) and 50° C. (6b) both in the presence and absence of 1 mM DTT.
Figure 6B:
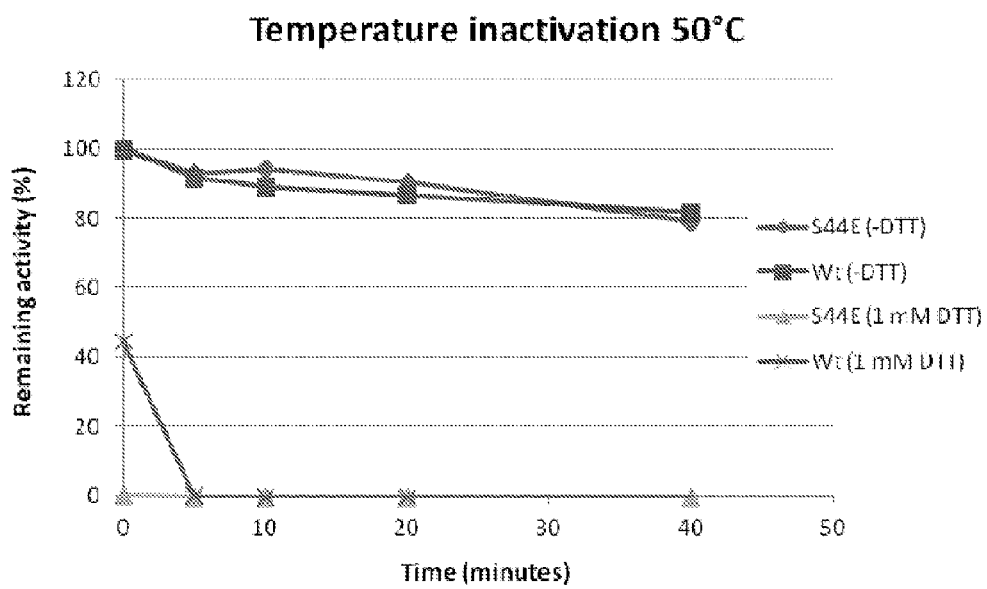
Figure 7:
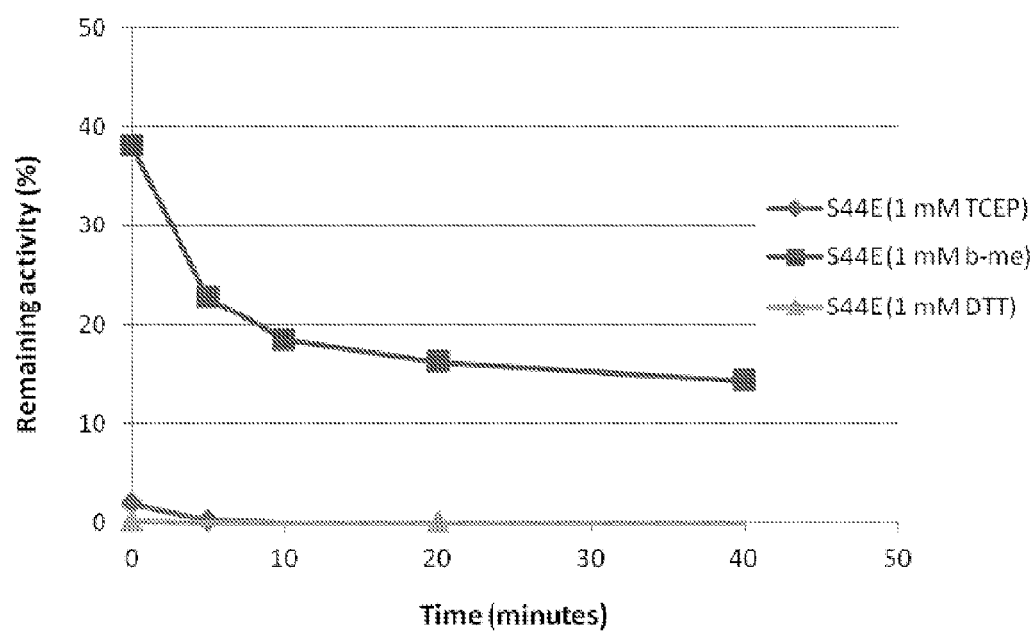
FIG. 7 shows the rate of VsEndA_S44E inactivation at 40° C. in the presence of 1 mM of one of the following inactivation additives: DTT, Tris(2-Carboxyethyl) phosphine (TCEP) and 2-mercaptoethanol.
Figure 8A:
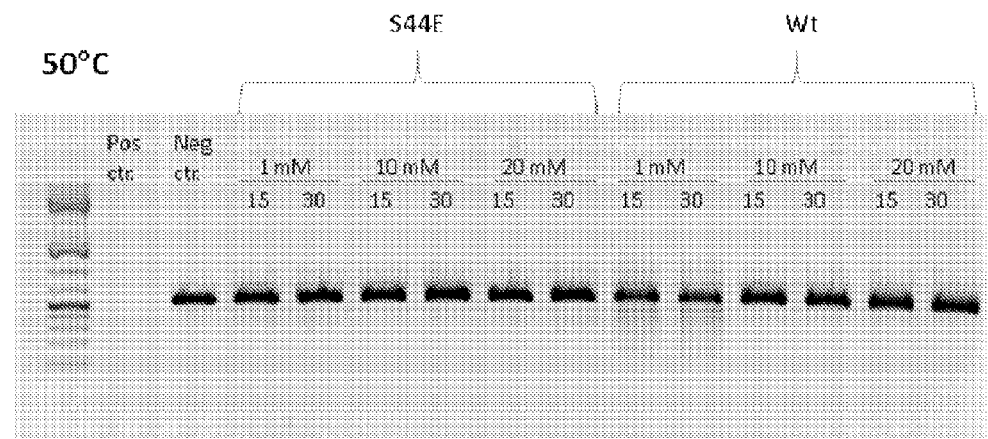
Figure 8B:
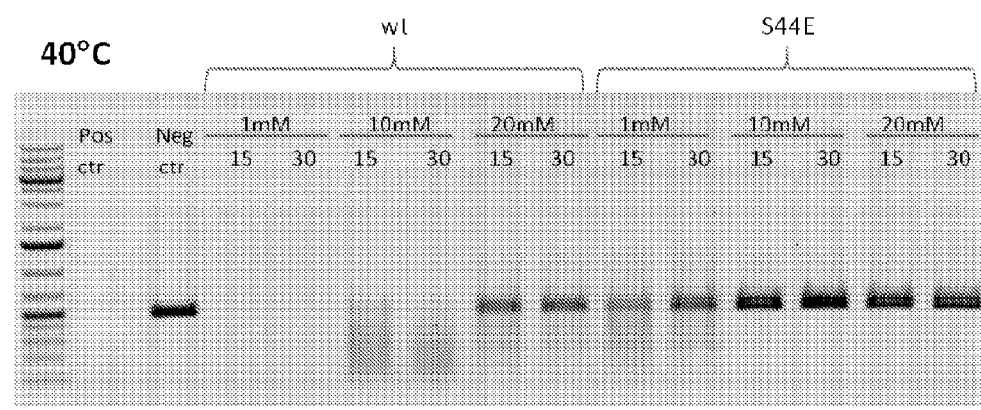
Figure 8C:
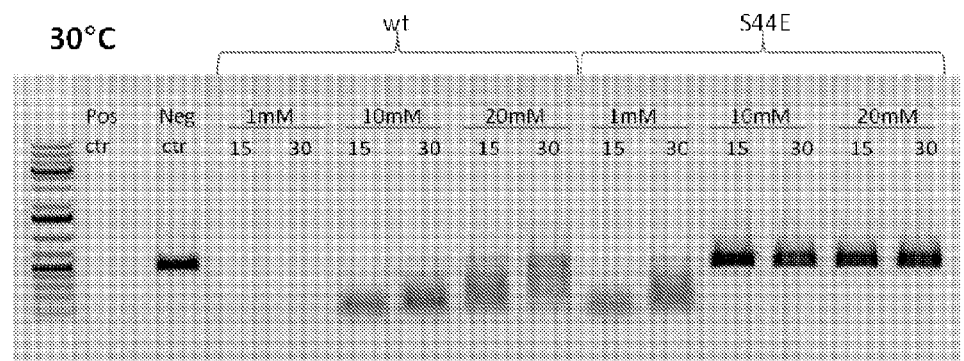
Figure 8D:
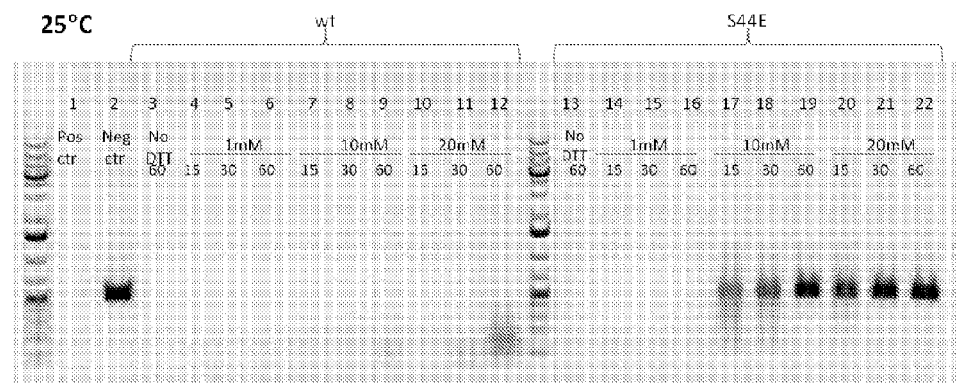

When comparing the data shown in FIG. 7 with that of FIG. 6a, it can be determined that all of the inactivation additives facilitated inactivation. DTT and TCEP were found to be more effective as inactivation additives compared to 2-mercaptoethanol. The VsEndA_S44E mutant has been shortened to "S44E" and the wild-type VsEndA to "wt" in the Figure legends.

Example 7

Heat Inactivation Experiments

To examine the temperature stability and to determine if it is possible to completely inactivate the VsEndA_S44E using heat, the integrity of a purified PCR-product in the presence of the heat-inactivated enzyme was assessed. This provided a more sensitive assay compared to the modified Kunitz assay described in Example 3, as it can test whether the inactivation is reversible upon decrease in temperature, or irreversible.

Enzyme (VsEndA_S44E or wild-type, VsEndA, 130 U/µl) in a 25 mM Tris/HCl pH 8.5, 0.5M NaCl, 5 mM MgCl$_2$ buffer was transferred to Eppendorf tubes in a total volume of 50 µl. Freshly made Dithiothreitol (DTT) were added to a final concentration of 1, 10 or 20 mM. Samples were heat inactivated for 15, 30 or 60 minutes at various temperatures. Tubes were placed on ice after the inactivation step.

Assay for determination of residual activity was performed by adding 5 µl of heat-inactivated enzyme to 500 ng of a 500 bp PCR-product in a buffer consisting of 25 mM Tris/HCl pH 8.5, 5 mM MgCl$_2$ and 0.5 M NaCl. Samples were incubated for 3 hours at 37° C. Where DTT was added to the enzyme preparation for inactivation, it was also present in the assay for residual activity.

Finally, to determine any degradation of the PCR-product, samples were analyzed on 1% agarose gel. A negative control (no enzyme) and a positive control (containing 6 U wt-enzyme) were treated in the same way as in the reactions above.

FIG. 8 summarise the heat-inactivation experiments of the VsEndA_S44E mutant compared to the wild type VsEndA enzyme at 50° C., 40° C., 30° C. and 25° C. The negative control shows the intact PCR-product, whereas the positive control illustrates the effect of approximately 1% residual activity. At 50° C., the VsEndA_S44E mutant enzyme was found to be completely inactivated after 15 minutes in the presence of 1 mM DTT, while the wild-type was only partially inactivated. At 40° C., 1 mM DTT was able to partially inactivate the VsEndA_S44E mutant after 15 minutes, compared to the 10 mM required to partially inactivate the VsEndA enzyme. At 25° C., DTT at a concentration of 20 mM or less was not able to fully inactivate the VsEndA enzyme after 60 minutes, whereas 10 mM of DTT was able to fully inactivate the VsEndA_S44E mutant after 60 minutes, demonstrating the effect of the substitution. The addition of at least 10 mM DTT is necessary for complete inactivation of the VsEndA_S44E mutant enzyme at 30° C. The VsEndA_S44E mutant has been shortened to "S44E" and the wild-type VsEndA to "wt" in the Figure legends.

In a further heat-inactivation experiment, the VsEndA_S44E mutant compared to the wild type VsEndA enzyme at 4° C., in the presence of either DTT or TCEP at a concentration of either 1 mM, 10 mM or 20 mM, using the same controls described above. As shown in FIG. 9, even at this low temperature, the presence of 10 mM DTT or TCEP was able to completely inactivate the VsEndA_S44E mutant after 6 hours. In comparison, even 20 mM DTT was not able to inactivate the wild type VsEndA enzyme after 18 hours of incubation. TCEP was shown to completely inactivate the VsEndA enzyme at this temperature either after 18 hours of incubation at a concentration of 10 mM or more or after 6 hours of incubation at a concentration of 20 mM.

Example 8

Heat Inactivation Experiments—Residual Activity in the Absence of TCEP

In this Example, we determined the conditions where inactivation of VsEndA_S44E is still observed after the removal of the inactivation additive.

This Example was carried out in a similar manner to Example 7 except that the inactivation additive TCEP was studied, and, after inactivation had taken place, the TCEP was removed by dialysis using Pur-A-Lyzer dialysis tubes (Sigma). The buffer was exchanged once during a two-day dialysis. Determination of residual activity was performed using a 1% agarose gel as described in Example 7.

A selection of optimal inactivation parameters determined from this study are presented in Table 5.

TABLE 5

Parameters required to achieve inactivation in VsEndA_S44E. Parameter (i) - concentration of the inactivation additive TCEP added to the endonuclease (mM), parameter (ii) - the inactivation temperature the endonuclease is heated to (in the presence of inactivation additive) (° C.), parameter (iii) - the time at which the endonuclease is incubated at the inactivation temperature (minutes), parameter (iv) - the temperature the endonuclease is stored at after cooling from the inactivation temperature (in the presence of the inactivation additive) (° C. or "RT" for room temperature) and parameter (v) the time at which the endonuclease is incubated at the storage temperature (days). "N/A" for parameters (ii) and (iii) apply when VsEndA_S44E is not heated to an inactivation temperature.

| Parameter | | | | |
|---|---|---|---|---|
| (i) (mM) | (ii) (° C.) | (iii) (min) | (iv) (° C.) | (v) (days) |
| 10 | 50 | 60 | RT | 2 |
| 10 | N/A | N/A | 37 | 1 |
| 10 | N/A | N/A | RT | 4 |
| 1 | 50 | 60 | 37 | 1 |

Example 9

Removal of Contaminating DNA from a DNA Polymerase Preparation

The ability of VsEndA_S44E to remove contaminating bacterial genomic DNA from commercial DNA polymerases in a typical polymerase buffer was tested. 0.14 U/µL Accustart (Quanta Biosciences), Tempase (VWR) or GoTaq (Promega) was treated with 28 U/µL VsEndA_S44E for 15 minutes at 37° C. in a buffer consisting of 10 mM Tris-HCl, 111 mM KCl, 5.6 mM MgCl$_2$. After incubation at 37° C. for 15 minutes, DTT was added to a final concentration of 10 mM and the samples were incubated at 40° C. for 30 minutes in order to inactivate the VsEndA_S44E mutant. Finally primers, probes and dNTPs were added and the final concentration of the components in the polymerase reaction mixture was: 25 mU/µL DNA polymerase, 300 nM of each primer, 200 nM probe, 100 µM dATP, dCTP, dGTP and 200 µM dUTP in a buffer composed of 10 mM Tris-HCl, 20 mM KCl, 5 mM MgCl$_2$.

The following controls were included: a) samples containing buffer instead of VsEndA_S44E, b) samples containing buffer and E. coli genomic DNA, c) samples where E. coli genomic DNA was added before VsEndA_S44E inactivation, and d) samples where E. coli genomic DNA was added after VsEndA_S44E inactivation. The qPCR was performed in 20 µl reactions in a Stratagene Mx3500P (Agilent technologies) and the thermal cycling conditions were as recommended by the manufacturers of the DNA polymerases.

VsEndA_S44E was able to remove contaminating bacterial genomic DNA from all the polymerases tested. FIG. 10 illustrates the effect of the VsEndA_S44E treatment of Accustart and GoTaq polymerases. The VsEndA_S44E mutant has been shortened to "S44E" in the Figure legends. The level of contaminating bacterial DNA was reduced and spiked E. coli genomic DNA was removed. There is no or minimal impairment of the polymerase function after VsEndA_S44E treatment.

Example 10

Removal of Contaminating DNA from a PCR Master Mix

Commercial quantitative PCR (qPCR) master mixes have been shown to contain trace amounts of contaminating bacterial genomic DNA. In this Example the ability of VsEndA_S44E to remove bacterial genomic DNA contaminants from commercial qPCR master mixes was tested. Maxima qPCR master mix (Fermentas) or Express qPCR Supermix Universal (Invitrogen) was treated with 25 U/µL VsEndA_S44E for 15 minutes at 37° C. S44E_End I was inactivated by adding 10 mM DTT (1-4 dithiothreitol) and incubating at 40° C. for 30 minutes. To test for the effect of the VsEndA_S44E treatment on the removal of contaminating DNA from the polymerase, one S44E_End I treated sample was analysed alongside the following controls: a) samples containing buffer instead of VsEndA_S44E, b) samples where E. coli genomic DNA was added before buffer, c) samples where E. coli genomic DNA was added after buffer, d) samples where E. coli genomic DNA was added before VsEndA_S44E inactivation, and e) samples where E. coli genomic DNA was added after VsEndA_S44E inactivation. Finally, primers and probe were added to a final concentration of 300 nM and 200 nM respectively. The primers and probe were targeted to the 16S rRNA gene of E. coli as described by Corless et al (J Clin Microbiol. 2000, 38(5):1747-52). The thermal cycling conditions were as follows: 50° C. for 2 min, 95° C. for 10 min followed by 45 cycles of 95° C. for 30 seconds, 60° C. for 30 seconds and 72° C. for 30 seconds. The qPCR was performed in 20 µl reactions in a Stratagene Mx3500P (Agilent technologies).

As illustrated in FIG. 11, VsEndA_S44E is able to decrease the level of contaminating genomic bacterial DNA in Maxima qPCR master mix. The VsEndA_S44E mutant has been shortened to "S44E" in the Figure legends. Furthermore, the addition of VsEndA_S44E to a master mix spiked with E. coli DNA results in the same QC-value as a VsEndA_S44E treated (non-spiked) master mix. S44E_End I is also able to remove some of the bacterial DNA contaminants contained in the master mix. The polymerase-reaction is not influenced by the VsEndA_S44E treatment. Thus, VsEndA_S44E is able to remove contaminating DNA, can be completely inactivated and the inactivated VsEndA_S44E does not impair the performance of the polymerase. Similar results were obtained with Express qPCR Supermix Universal (Life Technologies) (data not shown).

Example 11

Removal of Bacterial Genomic DNA from Polymerase Solutions of High Salinity

VsEndA_S44E treatment is particularly useful in purifications of proteins that must be free of nuclease activity as inactivation of VsEndA_S44E easily can be accomplished. Furthermore, in the purification of DNA-binding proteins, the use of a salt active nuclease is convenient as salt can be added to protein preparations to limit DNA-protein interactions. In this Example we tested the ability of VsEndA_S44E to remove DNA contaminations from a DNA polymerase in a solution of 0.5 and 1.0 M sodium chloride.

TEMPase Hot Start DNA Polymerase (VWR) in 25 mM Tris-HCl, 5 mM MgCl$_2$ and 0.5 M or 1.0 M NaCl were treated with 25 U/µL VsEndA_S44E for 15 minutes at 37° C. The following controls were analysed alongside the above sample: a) samples containing buffer instead of VsEndA_S44E, b) samples where 20 pg E. coli genomic DNA was added before buffer, and c) samples where 20 pg E. coli genomic DNA was added before VsEndA_S44E inactivation. VsEndA_S44E was inactivated by adding 10 mM DTT and incubating at 40° C. for 30 minutes. After the inactivation step the buffer of the samples were changed to a polymerase-buffer by using Zeba™Spin Desalting Columns with a cutoff of 7K (Thermo Scientific) according to the manufacturer's instructions. Finally primers and probe were added and the constituents of the polymerase buffer were as follows: 10 mM Tris-HCl, 20 mM KCl, 5 mM $MgCl_2$, 100 µM dATP, dCTP, dGTP and 200 µM dUTP, 300 nM of each primer and 200 nM of the probe. The thermal cycling conditions were as follows: 95° C. for 15 min followed by 45 cycles of 95° C. for 30 seconds and 60° C. for 30 seconds. The qPCR was performed in 20 µL reactions in a Stratagene Mx3500P (Agilent technologies).

FIG. 12 illustrate the VsEndA_S44E treatment in polymerase solutions containing 0.5 M and 1.0 M sodium chloride. The VsEndA_S44E mutant has been shortened to "S44E" in the Figure legends. These Figures show that the VsEndA_S44E mutant's ability to remove the spiked E. coli DNA from the polymerase solution was not affected by the high salinity.

In a separate study, the activity of the VsEndA_S44E mutant was assessed over a range of differing sodium chloride and potassium chloride concentrations. FIG. 14 illustrates that VsEndA_S44E has an optimum activity at about 0.5 M sodium chloride, but operates at a broad range of sodium chloride and potassium chloride concentrations.

In a further study, the enzymatic activity of the VsEndA_S44E mutant in degrading calf thymus DNA at a range of varying sodium chloride concentrations and pH levels was compared to the activity of commercially available Benzonase (Serratia marcescens) nuclease. FIG. 16 illustrates that VsEndA_S44E degrades DNA at a broader range of pH levels and sodium chloride concentrations compared to Benzonase.

In a further study, the enzymatic activity of the VsEndA_S44E mutant in degrading DNA from E. coli cell lysate at a range of varying sodium chloride concentrations was assessed. FIG. 17 illustrates that the VsEndA_S44E mutant was active at sodium chloride concentrations of 0.25 M to 1.0 M.

Example 12

Use of S44E EndA to Remove DNA from a Protein Purification Preparation

As VsEndA_S44E could be useful in protein purification schemes, particularly in the purification of DNA-binding proteins which must be free of nuclease activity and contaminating DNA, we tested the ability of VsEndA_S44E to remove genomic DNA from an E. coli extract containing a recombinantly expressed DNA-binding protein.

The recombinantly expressed protein in this Example was cod uracil-DNA glycosylase (cod UNG) which catalyzes the removal of uracil from uracil-containing DNA. E. coli cells containing the cod UNG were harvested, washed and then lysed by sonication in a Tris/HCl buffer (25 mM Tris/HCl pH 8.0, 10 mM NaCl, 1 mM EDTA, 1% glycerol) containing lysozyme. The cell extract was centrifuged and the supernatant was collected. The pH of the supernatant was adjusted to 8.5 before the following concentrations of NaCl were added: 0 M, 0.25 M, 0.5 M, 0.75 M or 1.0 M. $MgCl_2$ was also added at 10 mM before treatment with 50 U/µL VsEndA_S44E for 30 min at 37° C. VsEndA_S44E was then inactivated by adding 10 mM DTT and incubating at 40° C. for 30 min. Non-treated controls were also included. VsEndA_S44E treated supernatant (1 µL) was added in a 50 µl qPCR reaction containing TEMPase Hot Start DNA Polymerase (VWR) with the same PCR buffer composition and thermal cycling conditions as described earlier in Example 10.

As shown in FIG. 13, VsEndA_S44E was able to remove most of the genomic E. coli DNA (>99.5%) in samples containing 0.5 M NaCl or more, although a significant amount of DNA is still left in the lysate. In samples of relatively low salinity (0 M and 0.25 M NaCl), the Cq values are found to be the same for both the untreated and the VsEndA_S44E-treated samples. This suggests that the DNA within the sample is interacting with the protein, making it unavailable to both the VsEndA_S44E enzyme and the polymerase. In comparison, at higher NaCl concentrations (0.5 M, 0.75 M and 1.0 M) a clear difference in DNA levels is seen between the untreated samples and the samples containing the VsEndA_S44E mutant, suggesting that the NaCl make the DNA more available to both the VsEndA_S44E and the polymerase. This example demonstrates that VsEndA_S44E is ideal for removal of DNA from cell extracts containing recombinantly expressed DNA-binding proteins. The addition of salts reduces protein-DNA interactions making the DNA available for the salt-active VsEndA_S44E. Furthermore, VsEndA_S44E can easily be irreversibly inactivated, a feature which is important as preparations of DNA-binding proteins commonly need to be free of nuclease-activity.

Example 13

The Effect of the Inactivation Additive TCEP on PCR Quality

In this Example, we show the effect of TCEP on Tempase polymerase and Tempase Key buffer on PCR efficiency.

TCEP of varying concentrations were added to the PCR strips, before the rest of the PCR components were added. E. coli gDNA (100 fg) was used as template for a 23S primer/probe set. All samples were run in duplicates, and all qPCR reactions had a total volume of 20 µl. Tempase polymerase (VWR) in Tempase Key buffer and in "Arctic buffer" (final conc: 10 mM Tris HCl pH 8.3, 10 mM KCl and 5 mM $MgCl_2$) was tested, as well as the Agilent Brilliant III mastermix (Agilent Technologies).

The results from this study show that a TCEP concentration of 2.5 mM or below has no noticeable effect on PCR efficiency (data not shown).

Example 14

Stability of VsEndA_S44E Inactivation in Taq Polymerase Cleanups

The presence of TCEP may be necessary for keeping VsEndA_S44E inactive after inactivation procedures have been carried out. For this reason, we assessed the long term ability of TCEP to maintain the inactivation of VsEndA_S44E.

A buffer comprising 2 µL Tempase Key buffer, 0.8 µL dNTP/dUTP (2.5/5 mM), 0.2 µL Tempase (5 U/µL), 1 µL VsEndA_S44E storage-buffer/VsEndA_S44E (10 U/µL) and 1 µL water was mixed in a 17.5× volume and incubated at 37° C. for 25 minutes. After the DNA decontamination step VsEndA_S44E was inactivated by adding 1 µL 50 mM TCEP per 1×rx and incubating at 37° C. for 25 minutes. After inactivation, the mix were stored for 14 days at 4° C. (at an effective concentration of 8.3 mM TCEP). The treated mix was thereafter dispersed in qPCR strips and added E. coli 23S primers/probe and template (200 fg E. coli gDNA or no template) dissolved in 14 μL. The total volume of each qPCR mix was 20 μL. This dilution ensured that the concentration of TCEP was reduced to 2.5 mM, which, from the results of Example 13, was known not to affect PCR efficiency. The strips were stored at 4° C. for 4 hours in order to detect any loss of template caused by reactivated VsEndA_S44E before the qPCR was run. The qPCR was performed in a Stratagene Mx3500P (Agilent technologies) and the thermal cycling conditions were as follows: 50° C. for 2 minutes, 95° C. for 10 minutes followed by 45 cycles of 95° C., 60° C. for 30 seconds and 72° C. for 30 seconds.

The results show that there is no significant reactivation of VsEndA_S44E over a period of at least 2 weeks at 4° C. when stored in presence of the inactivation additive TCEP at a concentration of 8.3 mM (data not shown).

Example 15

The Performance of a Blend of VsEndA_S44E and VcEndA (Wild-Type) in Buffers with Varying Sodium Chloride Concentrations and pHs VsEndA_S44E has a pH-optimum of 8.5 and a sodium chloride concentration-optimum of 425 mM. A homologue of the wild-type *Vibrio salmonicida*-derived endonuclease (VsEndA) obtained from *Vibrio cholerae*, here referred to as VcEndA, has a broad pH range, with a pH optimum of 7.5 and a sodium chloride concentration-optimum of 175 mM. We therefore combined VsEndA_S44E and VcEndA in order to determine whether it would result in a nuclease product with a broad pH and sodium chloride concentration working range, together with favourable inactivation characteristics. Here we tested the performance of this enzyme composition in Tris-buffers with varying pHs and sodium chloride concentrations against the performance of Benzonase, the leading non-specific nuclease on the market.

A total of twenty 25 mM tris-buffers containing 5 mM MgCl$_2$ were made with combinations of different pHs and sodium chloride concentrations as depicted in the matrix shown Table 6.

TABLE 6

|        | 0M NaCl | 0.25M NaCl | 0.5M NaCl | 0.75M NaCl | 1.0M NaCl |
|--------|---------|------------|-----------|------------|-----------|
| pH 7   | 1       | 2          | 3         | 4          | 5         |
| pH 7.5 | 6       | 7          | 8         | 9          | 10        |
| pH 8.0 | 11      | 12         | 13        | 14         | 15        |
| pH 8.5 | 16      | 17         | 18        | 19         | 20        |

The blend of VsEndA_S44E and VcEndA was made by mixing the enzymes 1:1 (w/w) and the activity was measured in a 25 mM Tris-HCl-buffer pH 8 containing 250 mM sodium chloride. In 100 μL buffer containing 50 μg calf thymus DNA, 300 U enzyme was added and the reactions were incubated at 37° C. for 30 minutes. The reactions were stopped by adding an EDTA-containing loading dye and the samples were loaded on a 1% agarose-gel.

The results showed no significant deterioration of VsEndA_S44E/VcEndA composition activity at a sodium chloride concentration range of between 0 M and 1 M. In comparison, Benzonase showed some loss in activity at 0.25 M and above (data not shown). In addition, a composition comprising VsEndA_S44E and VcEndA showed complete inactivation after storage with 20 mM DTT or TCEP at 4° C. for 6 hours, whilst a composition comprising wild-type VsEndA and VcEndA did not show similar inactivation characteristics under these conditions (data not shown).

The invention claimed is:

1. An endonuclease I or enzymatically active fragment thereof wherein said endonuclease I is selected from the group consisting of (i) an endonuclease I having the sequence of SEQ ID NO. 4 and (ii) an endonuclease I having a sequence at least 90% identical to SEQ ID NO: 4, wherein the amino acid residue which is immediately N-terminal of the FYCGC pentapeptide motif in said endonuclease I or said active fragment has been substituted with a residue which is negatively charged.

2. The endonuclease I or enzymatically active fragment thereof of claim 1, wherein said negatively charged residue is selected from the group consisting of glutamic acid, aspartic acid, 4-Fluoro-DL-glutamic acid, γ-Carboxy-DL-glutamic acid and D-2-Aminoadipic acid.

3. The endonuclease I or enzymatically active fragment thereof of claim 2, wherein said negatively charged residue is glutamic acid.

4. The endonuclease I or enzymatically active fragment thereof of claim 1 which is derived from *Vibrio salmonicida*.

5. The endonuclease I or enzymatically active fragment thereof of claim 1 which is at least 95% inactivated when incubated for 30 minutes at 50° C. in the presence of 0.5 mM TCEP and residual activity is assessed in the presence of 0.5 mM TCEP.

6. The endonuclease I or enzymatically active fragment thereof of claim 1 which, at a concentration of 0.5 M sodium chloride, has a catalytic activity that is no less than 60% of the catalytic activity exhibited by said endonuclease I or enzymatically active fragment at its optimum salt concentration.

7. A method of removing contaminating polynucleotides from a sample, said method comprising contacting the sample with an endonuclease I or enzymatically active fragment thereof as defined in claim 1.

8. The method of claim 7 wherein the sample is contacted with the endonuclease I or enzymatically active fragment thereof under conditions which permit digestion of any polynucleotide therein and then the sample and endonuclease mixture are contacted with an inactivation additive at a temperature and for a time sufficient to inactivate said endonuclease.

9. The method of claim 7, wherein said sample is a preparation containing a recombinantly produced protein of interest.

10. The method of claim 7, wherein said sample contains an analyte protein of interest.

11. The method of claim 10 wherein the sample is derived from a cell lysate, tissue sample or body fluid.

12. The method of claim 7, wherein the sample comprises an antibody or antibody fragment.

13. The method of claim 7, wherein the sample comprises a DNA binding protein or a protein which associates with nucleic acids in solution.

14. The method of claim 7, wherein the sample is a reagent solution that may be used in a polynucleotide analysis technique.

15. The method of claim 8 wherein the inactivation additive is a metal ion chelating agent or a disulphide bond reducing agent.

16. The method of claim 15 wherein the agent is selected from the group consisting of ethylenediaminetetraacetic acid (EDTA) dithiothreitol 2-mercaptoethanol, 2-mercaptoethylamine.HCl, TCEP (Tris(2-Carboxyethyl) phosphine) and N-ethylmaleimide.

17. A composition comprising the endonuclease I or enzymatically active fragment thereof of claim 1 and a second endonuclease I.

18. The composition of claim 17 wherein the second endonuclease I has the sequence of SEQ ID NO. 5, or enzymatically active fragment thereof.

19. The composition of claim 18 wherein the second endonuclease I or enzymatically active fragment thereof is from *Vibrio cholerae*.

20. The method of claim 9, wherein said protein is an enzyme.

21. The method of claim 14, wherein said polynucleotide analysis technique is PCR or DNA/RNA sequencing.

* * * * *

SEQUENCE LISTING

```
<160> NUMBER OF SEQ ID NOS: 30

<210> SEQ ID NO 1
<211> LENGTH: 234
<212> TYPE: PRT
<213> ORGANISM: Vibrio salmonicida

<400> SEQUENCE: 1

Met Lys Leu Ile Arg Leu Val Ile Ser Leu Ile Ala Val Ser Phe Thr
1               5                   10                  15

Val Asn Val Met Ala Ala Pro Pro Ser Ser Phe Ser Lys Ala Lys Lys
            20                  25                  30

Glu Ala Val Lys Ile Tyr Leu Asp Tyr Pro Thr Ser Phe Tyr Cys Gly
        35                  40                  45

Cys Asp Ile Thr Trp Lys Asn Lys Lys Gly Ile Pro Glu Leu Glu
    50                  55                  60

Ser Cys Gly Tyr Gln Val Arg Lys Gln Glu Lys Arg Ala Ser Arg Ile
65                  70                  75                  80

Glu Trp Glu His Val Val Pro Ala Trp Gln Phe Gly His Gln Arg Gln
                85                  90                  95

Cys Trp Gln Lys Gly Gly Arg Lys Asn Cys Thr Arg Asn Asp Lys Gln
            100                 105                 110

Phe Lys Ser Met Glu Ala Asp Leu His Asn Leu Val Pro Ala Ile Gly
        115                 120                 125
```

Glu Val Asn Gly Asp Arg Ser Asn Phe Arg Phe Ser Gln Trp Asn Gly
    130                 135                 140

Ser Lys Gly Ala Phe Tyr Gly Gln Cys Ala Phe Lys Val Asp Phe Lys
145                 150                 155                 160

Gly Arg Val Ala Glu Pro Pro Ala Gln Ser Arg Gly Ala Ile Ala Arg
                165                 170                 175

Thr Tyr Leu Tyr Met Asn Asn Glu Tyr Lys Phe Asn Leu Ser Lys Ala
            180                 185                 190

Gln Arg Gln Leu Met Glu Ala Trp Asn Lys Gln Tyr Pro Val Ser Thr
        195                 200                 205

Trp Glu Cys Thr Arg Asp Glu Arg Ile Ala Lys Ile Gln Gly Asn His
    210                 215                 220

Asn Gln Phe Val Tyr Lys Ala Cys Thr Lys
225                 230

<210> SEQ ID NO 2
<211> LENGTH: 705
<212> TYPE: DNA
<213> ORGANISM: Artificial Sequence
<220> FEATURE:
<223> OTHER INFORMATION: cDNA

<400> SEQUENCE: 2
atgaaattaa ttcgcttagt tatcagtctt attgctgtca gtttcactgt taacgtaatg      60
gcagcacctc cttcttcttt ctcaaaagca aaaaagaag ccgtcaaaat ctatcttgat     120
tacccaaccg agttttattg tggctgtgac attacgtgga aaataaaaa gaaagggatc     180 cctgaattag aaagctgcgg ataccaagtc cgtaaacaag aaaaacgagc cagtcgtatt     240
gaatgggagc atgttgttcc agcatggcaa tttggtcatc aacgtcaatg ttggcaaaaa     300
ggtgggcgta aaattgcac tagaaacgac aagcaattca atcaatgga agccgactta      360 cataatctag tgcctgcgat tggtgaagta acgggaca gatccaactt ccgattctca      420
caatggaatg gaagcaaagg cgctttctat ggccaatgtg cttttaaagt cgacttcaaa     480
ggccgtgttg ccgagccacc agcacaatct cgtggtgcca ttgcccgaac gtatctttat     540
atgaacaacg aatataaatt taacttatca aaagcacagc gacaacttat ggaagcatgg     600
aacaaacagt atccagtatc aacttgggaa tgtactcgtg atgaacgtat agcaaaaatc     660
caaggcaatc ataatcaatt tgtttataaa gcatgcacta aataa                    705

<210> SEQ ID NO 3
<211> LENGTH: 231
<212> TYPE: PRT
<213> ORGANISM: Vibrio cholerae

<400> SEQUENCE: 3

Met Met Ile Phe Arg Phe Val Thr Thr Leu Ala Ala Ser Leu Pro Leu
1               5                   10                  15

Leu Thr Phe Ala Ala Pro Ile Ser Phe Ser His Ala Lys Asn Glu Ala
            20                  25                  30

Val Lys Ile Tyr Arg Asp His Pro Val Ser Phe Tyr Cys Gly Cys Glu
        35                  40                  45

Ile Arg Trp Gln Gly Lys Lys Gly Ile Pro Asp Leu Glu Ser Cys Gly
    50                  55                  60

Tyr Gln Val Arg Lys Asn Glu Asn Arg Ala Ser Arg Ile Glu Trp Glu
65                  70                  75                  80

-continued

His Val Val Pro Ala Trp Gln Phe Gly His Gln Leu Gln Cys Trp Gln
                85                  90                  95

Gln Gly Gly Arg Lys Asn Cys Thr Arg Thr Ser Pro Glu Phe Asn Gln
            100                 105                 110

Met Glu Ala Asp Leu His Asn Leu Thr Pro Ala Ile Gly Glu Val Asn
        115                 120                 125

Gly Asn Arg Ser Asn Phe Ser Phe Ser Gln Trp Asn Gly Ile Asp Gly
    130                 135                 140

Val Thr Tyr Gly Gln Cys Glu Met Gln Val Asn Phe Lys Glu Arg Thr
145                 150                 155                 160

Ala Met Pro Pro Glu Arg Ala Arg Gly Ala Ile Ala Arg Thr Tyr Leu
                165                 170                 175

Tyr Met Ser Glu Gln Tyr Gly Leu Arg Leu Ser Lys Ala Gln Asn Gln
            180                 185                 190

Leu Met Gln Ala Trp Asn Asn Gln Tyr Pro Val Ser Glu Trp Glu Cys
        195                 200                 205

Val Arg Asp Gln Lys Ile Glu Lys Val Gln Gly Asn Ser Asn Arg Phe
    210                 215                 220

Val Arg Glu Gln Cys Pro Asn
225                 230

<210> SEQ ID NO 4
<211> LENGTH: 213
<212> TYPE: PRT
<213> ORGANISM: Vibrio salmonicida

<400> SEQUENCE: 4

Ala Pro Pro Ser Ser Phe Ser Lys Ala Lys Lys Glu Ala Val Lys Ile
1               5                   10                  15

Tyr Leu Asp Tyr Pro Thr Ser Phe Tyr Cys Gly Cys Asp Ile Thr Trp
            20                  25                  30

Lys Asn Lys Lys Lys Gly Ile Pro Glu Leu Glu Ser Cys Gly Tyr Gln
        35                  40                  45

Val Arg Lys Gln Glu Lys Arg Ala Ser Arg Ile Glu Trp Glu His Val
    50                  55                  60

Val Pro Ala Trp Gln Phe Gly His Gln Arg Gln Cys Trp Gln Lys Gly
65                  70                  75                  80

Gly Arg Lys Asn Cys Thr Arg Asn Asp Lys Gln Phe Lys Ser Met Glu
                85                  90                  95

Ala Asp Leu His Asn Leu Val Pro Ala Ile Gly Glu Val Asn Gly Asp
            100                 105                 110

Arg Ser Asn Phe Arg Phe Ser Gln Trp Asn Gly Ser Lys Gly Ala Phe
        115                 120                 125

Tyr Gly Gln Cys Ala Phe Lys Val Asp Phe Lys Gly Arg Val Ala Glu
    130                 135                 140

Pro Pro Ala Gln Ser Arg Gly Ala Ile Ala Arg Thr Tyr Leu Tyr Met
145                 150                 155                 160

Asn Asn Glu Tyr Lys Phe Asn Leu Ser Lys Ala Gln Arg Gln Leu Met
                165                 170                 175

Glu Ala Trp Asn Lys Gln Tyr Pro Val Ser Thr Trp Glu Cys Thr Arg
            180                 185                 190

Asp Glu Arg Ile Ala Lys Ile Gln Gly Asn His Asn Gln Phe Val Tyr
        195                 200                 205

Lys Ala Cys Thr Lys
    210

<210> SEQ ID NO 5
<211> LENGTH: 211
<212> TYPE: PRT
<213> ORGANISM: Vibrio cholerae

<400> SEQUENCE: 5

Ala Pro Ile Ser Phe Ser His Ala Lys Asn Glu Ala Val Lys Ile Tyr
1               5                   10                  15

Arg Asp His Pro Val Ser Phe Tyr Cys Gly Cys Glu Ile Arg Trp Gln
            20                  25                  30

Gly Lys Lys Gly Ile Pro Asp Leu Glu Ser Cys Gly Tyr Gln Val Arg
        35                  40                  45

Lys Asn Glu Asn Arg Ala Ser Arg Ile Glu Trp Glu His Val Val Pro
    50                  55                  60

Ala Trp Gln Phe Gly His Gln Leu Gln Cys Trp Gln Gly Gly Arg
65                  70                  75                  80

Lys Asn Cys Thr Arg Thr Ser Pro Glu Phe Asn Gln Met Glu Ala Asp
                85                  90                  95

Leu His Asn Leu Thr Pro Ala Ile Gly Glu Val Asn Gly Asn Arg Ser
            100                 105                 110

Asn Phe Ser Phe Ser Gln Trp Asn Gly Ile Asp Gly Val Thr Tyr Gly
        115                 120                 125

Gln Cys Glu Met Gln Val Asn Phe Lys Glu Arg Thr Ala Met Pro Pro
    130                 135                 140

Glu Arg Ala Arg Gly Ala Ile Ala Arg Thr Tyr Leu Tyr Met Ser Glu
145                 150                 155                 160

Gln Tyr Gly Leu Arg Leu Ser Lys Ala Gln Asn Gln Leu Met Gln Ala
                165                 170                 175

Trp Asn Asn Gln Tyr Pro Val Ser Glu Trp Glu Cys Val Arg Asp Gln
            180                 185                 190

Lys Ile Glu Lys Val Gln Gly Asn Ser Asn Arg Phe Val Arg Glu Gln
        195                 200                 205

Cys Pro Asn
    210

<210> SEQ ID NO 6
<211> LENGTH: 234
<212> TYPE: PRT
<213> ORGANISM: Artificial Sequence
<220> FEATURE:
<223> OTHER INFORMATION: Mutated Vibrio salmonicida peptide

<400> SEQUENCE: 6

Met Lys Leu Ile Arg Leu Val Ile Ser Leu Ile Ala Val Ser Phe Thr
1               5                   10                  15

Val Asn Val Met Ala Ala Pro Pro Ser Ser Phe Ser Lys Ala Lys Lys
            20                  25                  30

Glu Ala Val Lys Ile Tyr Leu Asp Tyr Pro Thr Glu Phe Tyr Cys Gly
        35                  40                  45

Cys Asp Ile Thr Trp Lys Asn Lys Lys Gly Ile Pro Glu Leu Glu
    50                  55                  60

Ser Cys Gly Tyr Gln Val Arg Lys Gln Glu Lys Arg Ala Ser Arg Ile
65                  70                  75                  80

Glu Trp Glu His Val Val Pro Ala Trp Gln Phe Gly His Gln Arg Gln
                85                  90                  95

```
Cys Trp Gln Lys Gly Gly Arg Lys Asn Cys Thr Arg Asn Asp Lys Gln
                100                 105                 110

Phe Lys Ser Met Glu Ala Asp Leu His Asn Leu Val Pro Ala Ile Gly
        115                 120                 125

Glu Val Asn Gly Asp Arg Ser Asn Phe Arg Phe Ser Gln Trp Asn Gly
    130                 135                 140

Ser Lys Gly Ala Phe Tyr Gly Gln Cys Ala Phe Lys Val Asp Phe Lys
145                 150                 155                 160

Gly Arg Val Ala Glu Pro Ala Gln Ser Arg Gly Ala Ile Ala Arg
                165                 170                 175

Thr Tyr Leu Tyr Met Asn Asn Glu Tyr Lys Phe Asn Leu Ser Lys Ala
                180                 185                 190

Gln Arg Gln Leu Met Glu Ala Trp Asn Lys Gln Tyr Pro Val Ser Thr
        195                 200                 205

Trp Glu Cys Thr Arg Asp Glu Arg Ile Ala Lys Ile Gln Gly Asn His
        210                 215                 220

Asn Gln Phe Val Tyr Lys Ala Cys Thr Lys
225                 230

<210> SEQ ID NO 7
<211> LENGTH: 218
<212> TYPE: PRT
<213> ORGANISM: Oceanimonas sp.

<400> SEQUENCE: 7

Gly Glu Ala Met Ser Phe Arg Gln Ala Lys Lys Val Ala Pro Gly Ile
1               5                   10                  15

Tyr Asn Asp Asn Leu Lys Thr Phe Tyr Cys Gly Cys Asn Ile Asp Thr
                20                  25                  30

Gln Gly Lys Lys Leu Val Pro Asp Leu Ala Gly Cys Gly Tyr Gln Val
            35                  40                  45

Arg Lys Gln Gln Gln Arg Ala Ser Arg Ile Glu Trp Glu His Val Val
    50                  55                  60

Pro Ala Trp Glu Phe Gly His Gln Arg Gln Cys Trp Gln Gln Gly Gly
65                  70                  75                  80

Arg Lys Asn Cys Thr Arg Lys Asp Glu Leu Phe Arg Gln Met Glu Gly
                85                  90                  95

Asp Leu His Asn Leu Val Pro Ala Val Gly Glu Val Asn Gly Asp Arg
                100                 105                 110

Ser Asn Tyr Arg Phe Ser Glu Trp Asn Gly Lys Pro Val Gln Tyr Gly
            115                 120                 125

Gln Cys Gln Met Leu Val Asp Phe Lys Gly Arg Lys Val Gln Pro Pro
    130                 135                 140

Glu Gln Ser Arg Gly Ala Ile Ala Arg Thr Tyr Leu Tyr Met Gln Gln
145                 150                 155                 160

Gln Tyr Arg Leu Lys Ile Ala Arg Gln Gln Gln Lys Leu Phe Glu Ala
                165                 170                 175

Trp Asn Arg Gln Tyr Pro Ala Ser Pro Trp Glu Cys Glu Arg Asp Asn
                180                 185                 190

Arg Ile Ser Arg Ile Gln Gly Asn His Asn Pro Phe Val Gln Glu Gln
            195                 200                 205

Cys Lys Asn Tyr Ala Tyr Thr Pro Asn Pro
210                 215

<210> SEQ ID NO 8
```

```
<211> LENGTH: 213
<212> TYPE: PRT
<213> ORGANISM: Salmonella sp.

<400> SEQUENCE: 8
```

Asp Gly Ile Asn Asn Phe Ser Gln Ala Lys Ala Ser Val Lys Val
1               5                   10                  15

Asn Ala Asp Ala Pro Gly Ser Phe Tyr Cys Gly Cys Gln Ile Arg Trp
                20                  25                  30

Gln Gly Lys Lys Gly Val Val Asp Leu Glu Ser Cys Gly Tyr Lys Val
            35                  40                  45

Arg Lys Asn Glu Asn Arg Ala Arg Arg Ile Glu Trp Glu His Val Val
        50                  55                  60

Pro Ala Trp Gln Phe Gly His Gln Arg Gln Cys Trp Gln Asp Gly Gly
65                  70                  75                  80

Arg Lys Asn Cys Ala Lys Asp Pro Val Tyr Arg Lys Met Glu Ser Asp
                85                  90                  95

Met His Asn Leu Gln Pro Ala Ile Gly Glu Val Asn Gly Asp Arg Gly
            100                 105                 110

Asn Phe Met Tyr Ser Gln Trp Asn Gly Gly Glu Gly Gln Tyr Gly Gln
        115                 120                 125

Cys Ala Met Lys Val Asp Phe Lys Ala Lys Leu Ala Glu Pro Pro Ala
130                 135                 140

Arg Ala Arg Gly Ala Ile Ala Arg Thr Tyr Phe Tyr Met Arg Asp Gln
145                 150                 155                 160

Tyr Gln Leu Lys Leu Ser Arg Gln Gln Thr Gln Leu Phe Asn Val Trp
                165                 170                 175

Asp Lys Gln Tyr Pro Val Thr Ala Trp Glu Cys Glu Arg Asp Ala Arg
            180                 185                 190

Ile Ala Lys Val Gln Gly Asn His Asn Pro Tyr Val Gln Arg Ala Cys
        195                 200                 205

Gln Ala Arg Lys Ser
        210

```
<210> SEQ ID NO 9
<211> LENGTH: 213
<212> TYPE: PRT
<213> ORGANISM: Enterobacter sp.

<400> SEQUENCE: 9
```

Asp Gly Ile Asn Ser Phe Ser Gln Ala Lys Ala Gly Val Lys Val
1               5                   10                  15

Asn Ala Asp Val Pro Gly Asp Phe Tyr Cys Gly Cys Lys Ile Asn Trp
                20                  25                  30

Gln Gly Lys Lys Gly Ile Val Asp Leu Glu Ser Cys Gly Tyr Lys Val
            35                  40                  45

Arg Lys Asn Glu Asn Arg Ala Ser Arg Ile Glu Trp Glu His Val Val
        50                  55                  60

Pro Ala Trp Gln Phe Gly His Gln Arg Gln Cys Trp Gln Asp Gly Gly
65                  70                  75                  80

Arg Lys Asn Cys Ala Lys Asp Pro Val Tyr Arg Gln Met Glu Ser Asp
                85                  90                  95

Met His Asn Leu Gln Pro Ala Val Gly Glu Val Asn Gly Asp Arg Gly
            100                 105                 110

Asn Phe Met Tyr Ser Gln Trp Asn Gly Gly Glu Gly Gln Tyr Gly Gln
        115                 120                 125

```
Cys Gly Met Lys Val Asp Phe Lys Glu Lys Val Ala Glu Pro Ala
        130                 135                 140

Arg Ala Arg Gly Ser Ile Ala Arg Thr Tyr Phe Tyr Met Arg Asp Arg
145                 150                 155                 160

Tyr Asn Leu Asn Leu Ser Arg Gln Gln Thr Gln Leu Phe Asn Ala Trp
                165                 170                 175

Asn Lys Gln Tyr Pro Val Thr Glu Trp Glu Cys Gln Arg Asp Glu Arg
                180                 185                 190

Ile Ala Arg Val Gln Gly Asn His Asn Pro Tyr Val Gln Arg Ala Cys
            195                 200                 205

Gln Ala Gln Lys Ser
        210
```

<210> SEQ ID NO 10
<211> LENGTH: 213
<212> TYPE: PRT
<213> ORGANISM: Yokenella sp.

<400> SEQUENCE: 10

```
Glu Gly Ile Asn Ser Phe Ser Gln Ala Lys Ala Gly Val Lys Val
1               5                   10                  15

Asn Ala Asp Val Ala Gly Asp Phe Tyr Cys Gly Cys Lys Ile Asn Trp
                20                  25                  30

Gln Gly Lys Lys Gly Val Val Asp Leu Glu Ser Cys Gly Tyr Lys Val
            35                  40                  45

Arg Lys Asn Glu Asn Arg Ala Ser Arg Ile Glu Trp Glu His Val Val
50                  55                  60

Pro Ala Trp Gln Phe Gly His Gln Arg Gln Cys Trp Gln Asp Gly Gly
65                  70                  75                  80

Arg Lys Asn Cys Gly Lys Asp Pro Val Tyr Arg Gln Met Glu Ser Asp
                85                  90                  95

Met His Asn Leu Gln Pro Ala Val Gly Glu Val Asn Gly Asp Arg Gly
            100                 105                 110

Asn Phe Met Tyr Ser Gln Trp Asn Gly Gly Glu Gly Gln Tyr Gly Gln
        115                 120                 125

Cys Ala Met Lys Val Asp Phe Lys Gly Lys Val Ala Glu Pro Ala
    130                 135                 140

Arg Ala Arg Gly Ala Ile Ala Arg Thr Tyr Phe Tyr Met Arg Asp Arg
145                 150                 155                 160

Tyr Gln Leu Ala Leu Ser Arg Gln Gln Thr Gln Leu Phe Asn Ala Trp
                165                 170                 175

Asp Lys Gln Tyr Pro Val Ser Glu Trp Glu Cys Glu Arg Asp Glu Arg
                180                 185                 190

Ile Ala Lys Tyr Gln Gly Asn His Asn Pro Tyr Val Gln Arg Ala Cys
            195                 200                 205

Gln Ala Gln Lys Ser
        210
```

<210> SEQ ID NO 11
<211> LENGTH: 213
<212> TYPE: PRT
<213> ORGANISM: Klebsiella sp.

<400> SEQUENCE: 11

```
Ala Gly Ile Asn Ser Phe Ser Gln Ala Lys Ala Gly Val Lys Val
1               5                   10                  15
```

Asn Ala Asp Val Pro Gly Asp Phe Tyr Cys Gly Cys Lys Ile Asp Trp
            20                  25                  30

Gln Gly Lys Lys Gly Val Ile Asp Leu Glu Ser Cys Gly Tyr Lys Val
        35                  40                  45

Arg Lys Asn Glu Asn Arg Ala Ser Arg Val Glu Trp Glu His Val Val
50                  55                  60

Pro Ala Trp Gln Phe Gly His Gln Arg Gln Cys Trp Gln Glu Gly Gly
65                  70                  75                  80

Arg Lys Asn Cys Ala Lys Asp Pro Glu Tyr Arg Lys Met Glu Ser Asp
                85                  90                  95

Met His Asn Leu Gln Pro Ala Val Gly Glu Val Asn Gly Asp Arg Gly
            100                 105                 110

Asn Phe Met Tyr Ser Gln Trp Asn Gly Gly Glu Gly Gln Tyr Gly Gln
        115                 120                 125

Cys Thr Met Lys Val Asp Phe Lys Asp Lys Ile Ala Glu Pro Pro Ala
130                 135                 140

Arg Ala Arg Gly Ala Ile Ala Arg Thr Tyr Phe Tyr Met Arg Asp Arg
145                 150                 155                 160

Tyr Gln Leu Asn Leu Ser Arg Gln Gln Thr Gln Leu Phe Thr Ala Trp
                165                 170                 175

Asn Lys Gln Tyr Pro Val Thr Ala Trp Glu Cys Glu Arg Asp Glu Arg
            180                 185                 190

Ile Ala Lys Val Gln Gly Asn His Asn Pro Tyr Val Gln Gln Ala Cys
        195                 200                 205

Gln Ala Gln Lys Ser
    210

<210> SEQ ID NO 12
<211> LENGTH: 213
<212> TYPE: PRT
<213> ORGANISM: Escherichia coli

<400> SEQUENCE: 12

Glu Gly Ile Asn Ser Phe Ser Gln Ala Lys Ala Val Ala Val Lys Ile
1               5                   10                  15

His Ala Asp Ala Pro Gly Thr Phe Tyr Cys Gly Cys Lys Ile Asp Trp
            20                  25                  30

Gln Gly Lys Lys Gly Val Val Asp Leu Gln Ser Cys Gly Tyr Gln Val
        35                  40                  45

Arg Lys Asn Glu Asn Arg Ala Ser Arg Val Glu Trp Glu His Val Val
50                  55                  60

Pro Ala Trp Gln Phe Gly His Gln Arg Gln Cys Trp Gln Asp Gly Gly
65                  70                  75                  80

Arg Lys Asn Cys Ala Lys Asp Pro Val Tyr Arg Lys Met Glu Ser Asp
                85                  90                  95

Met His Asn Leu Gln Pro Ser Val Gly Glu Val Asn Gly Asp Arg Gly
            100                 105                 110

Asn Phe Met Tyr Ser Gln Trp Asn Gly Gly Glu Gly Gln Tyr Gly Gln
        115                 120                 125

Cys Ala Met Lys Val Asp Phe Lys Glu Lys Val Ala Glu Pro Pro Ala
130                 135                 140

Arg Ala Arg Gly Ala Ile Ala Arg Thr Tyr Phe Tyr Met Arg Asp Gln
145                 150                 155                 160

Tyr Asn Leu Thr Leu Ser Arg Gln Gln Thr Gln Leu Phe Asn Ala Trp

```
                    165                 170                 175
Asn Lys Met Tyr Pro Val Thr Asp Trp Glu Cys Glu Arg Asp Glu Arg
            180                 185                 190

Ile Ala Lys Val Gln Gly Asn His Asn Pro Tyr Val Gln Arg Ala Cys
        195                 200                 205

Gln Ala Arg Lys Ser
    210

<210> SEQ ID NO 13
<211> LENGTH: 213
<212> TYPE: PRT
<213> ORGANISM: Shigella sp.

<400> SEQUENCE: 13

Glu Gly Ile Asn Ser Phe Ser Gln Ala Lys Ala Ala Val Lys Val
1               5                   10                  15

His Ala Asp Ala Pro Gly Thr Phe Tyr Cys Gly Cys Lys Ile Asn Trp
            20                  25                  30

Gln Gly Lys Lys Gly Val Val Asp Leu Gln Ser Cys Gly Tyr Gln Val
        35                  40                  45

Arg Lys Asn Glu Asn Arg Ala Ser Arg Val Glu Trp Glu His Val Val
50                  55                  60

Pro Ala Trp Gln Phe Gly His Gln Arg Gln Cys Trp Gln Asp Gly Gly
65                  70                  75                  80

Arg Lys Asn Cys Ala Lys Asp Pro Val Tyr Arg Lys Met Glu Ser Asp
                85                  90                  95

Met His Asn Leu Gln Pro Ser Val Gly Glu Val Asn Gly Asp Arg Gly
            100                 105                 110

Asn Phe Met Tyr Ser Gln Trp Asn Gly Gly Glu Gly Tyr Gly Gln
        115                 120                 125

Cys Ala Met Lys Val Asp Phe Lys Glu Lys Ala Ala Glu Pro Pro Ala
130                 135                 140

Arg Ala Arg Gly Ala Ile Ala Arg Thr Tyr Phe Tyr Met Arg Asp Gln
145                 150                 155                 160

Tyr Asn Leu Thr Leu Ser Arg Gln Gln Thr Gln Leu Phe Asn Ala Trp
                165                 170                 175

Asn Lys Met Tyr Pro Val Thr Asp Trp Glu Cys Glu Arg Asp Glu Arg
            180                 185                 190

Ile Ala Lys Val Gln Gly Asn His Asn Pro Tyr Val Gln Arg Ala Cys
        195                 200                 205

Gln Ala Arg Lys Ser
    210

<210> SEQ ID NO 14
<211> LENGTH: 213
<212> TYPE: PRT
<213> ORGANISM: Citrobacter sp.

<400> SEQUENCE: 14

Glu Gly Ile Asn Ser Phe Ser Gln Ala Lys Ala Ala Gly Val Lys Val
1               5                   10                  15

Asn Ala Asp Ala Pro Gly Asp Phe Tyr Cys Gly Cys Lys Ile Asn Trp
            20                  25                  30

Gln Gly Lys Lys Gly Val Val Asp Leu Glu Ser Cys Gly Tyr Lys Val
        35                  40                  45

Arg Lys Asn Glu Asn Arg Ala Ser Arg Ile Glu Trp Glu His Val Val
```

```
            50                  55                  60
Pro Ala Trp Gln Phe Gly His Gln Arg Gln Cys Trp Gln Asp Gly Gly
 65                  70                  75                  80

Arg Lys Asn Cys Ala Lys Asp Pro Val Tyr Arg Lys Met Glu Ser Asp
                 85                  90                  95

Met His Asn Leu Gln Pro Ala Val Gly Glu Val Asn Gly Asp Arg Ala
            100                 105                 110

Asn Phe Met Tyr Ser Gln Trp Asn Gly Glu Gly Gln Tyr Gly Gln
        115                 120                 125

Cys Ala Met Lys Val Asp Phe Lys Glu Lys Val Ala Glu Pro Pro Ala
            130                 135                 140

Arg Ala Arg Gly Ala Ile Ala Arg Thr Tyr Phe Tyr Met Arg Asp Gln
145                 150                 155                 160

Tyr Ser Leu Thr Leu Ser Arg Gln Gln Thr Gln Leu Phe Asn Ala Trp
                165                 170                 175

Asn Lys Gln Tyr Pro Val Thr Asp Trp Glu Cys Glu Arg Asp Glu Arg
            180                 185                 190

Ile Ala Lys Val Gln Gly Asn His Asn Pro Tyr Val Gln Arg Ala Cys
            195                 200                 205

Gln Ala Gln Lys Ser
    210

<210> SEQ ID NO 15
<211> LENGTH: 214
<212> TYPE: PRT
<213> ORGANISM: Cronobacter sp.

<400> SEQUENCE: 15

Ala Ser Gly Ile His Ser Phe Ser Gln Ala Lys Ala Ala Gly Val Lys
 1               5                  10                  15

Ile Asn Ala Asp Ala Pro Gly Asp Phe Tyr Cys Gly Cys Pro Ile Thr
                20                  25                  30

Trp Gln Gly Lys Lys Gly Ile Pro Asp Leu Lys Ala Cys Gly Tyr Gln
            35                  40                  45

Val Arg Lys Asn Glu Asn Arg Ala Ser Arg Ile Glu Trp Glu His Val
 50                  55                  60

Val Pro Ala Trp Gln Phe Gly His Gln Arg Gln Cys Trp Gln Asn Gly
 65                  70                  75                  80

Gly Arg Lys Asn Cys Asp Lys Asp Pro Val Tyr Arg Glu Met Glu Thr
                 85                  90                  95

Asp Leu His Asn Leu Gln Pro Ala Val Gly Glu Val Asn Gly Asp Arg
            100                 105                 110

Gly Asn Phe Leu Tyr Ser Gln Trp Arg Gly Gly Glu Gly Gln Tyr Gly
        115                 120                 125

Gln Cys Glu Met Lys Val Asp Phe Lys Asn Lys Gln Ala Glu Pro Pro
    130                 135                 140

Ala Arg Ala Arg Gly Ala Ile Ala Arg Thr Tyr Phe Tyr Met Arg Asp
145                 150                 155                 160

Lys Tyr Gln Leu Asn Leu Ser Arg Ala Gln Thr Gln Leu Phe Glu Ala
                165                 170                 175

Trp Asn Lys Leu Tyr Pro Val Thr Pro Trp Glu Cys Thr Arg Asp Glu
            180                 185                 190

Arg Ile Ala Lys Val Gln Gly Asn His Asn Pro Tyr Val Gln Gln Ala
            195                 200                 205
```

```
Cys Gln Gly Gln Asn Arg
    210
```

<210> SEQ ID NO 16
<211> LENGTH: 226
<212> TYPE: PRT
<213> ORGANISM: Rahnella sp.

<400> SEQUENCE: 16

```
Ile Gly Ala Leu Val Pro Leu Ser Ala Phe Ser Gln Ser Gly Asn Thr
1               5                   10                  15

Ile Asn Asn Phe Ser Gln Ala Lys Ala Ala Val Lys Ile Asn Gln
                20                  25                  30

Gly Ala Pro Thr Phe Tyr Cys Gly Cys Asn Ile Arg Trp Gln Gly Lys
            35                  40                  45

Lys Gly Thr Pro Asp Leu Gln Ser Cys Gly Tyr Ala Val Arg Lys Ser
    50                  55                  60

Glu Leu Arg Ala Ser Arg Ile Glu Trp Glu His Val Val Pro Ala Trp
65                  70                  75                  80

Gln Phe Gly His Gln Met Gln Cys Trp Gln Asp Gly Gly Arg Lys Asn
                85                  90                  95

Cys Ala Lys Asn Ala Asp Tyr Arg Gln Val Glu Thr Asp Leu His Asn
            100                 105                 110

Leu Glu Pro Ala Ile Gly Glu Val Asn Gly Asp Arg Asn Asn Phe Met
        115                 120                 125

Tyr Ser Gln Trp Asn Gly Gly Glu Gly Gln Tyr Gly Arg Cys Glu Met
    130                 135                 140

Lys Ile Asp Phe Lys Ala Lys Ala Ala Glu Pro Pro Ala Arg Ala Arg
145                 150                 155                 160

Gly Ala Ile Ala Arg Thr Tyr Phe Tyr Met Arg Asp Gln Tyr Lys Leu
                165                 170                 175

Asn Leu Ser Arg Gln Gln Thr Gln Leu Phe Thr Ala Trp Asp Arg Gln
            180                 185                 190

Tyr Pro Val Thr Ala Trp Glu Cys Glu Arg Asp Asn Arg Ile Ala Arg
        195                 200                 205

Val Gln Gly Asn His Asn Pro Tyr Val Gln Gln Ala Cys Ala Gln Arg
    210                 215                 220

Lys Ser
225
```

<210> SEQ ID NO 17
<211> LENGTH: 223
<212> TYPE: PRT
<213> ORGANISM: Erwinia sp.

<400> SEQUENCE: 17

```
Phe Pro Pro Leu Phe Cys His Ala Leu Ser Gln Gly Asn Tyr Gln Gln
1               5                   10                  15

Asn Asn Phe Ser Gln Ala Lys Ala Trp Ala Ala Gln Ile His His Asp
                20                  25                  30

Ala Pro Gly Thr Phe Tyr Cys Gly Cys Lys Ile Asp Trp Gln Gly Lys
            35                  40                  45

Lys Gly Val Pro Asp Leu Thr Ser Cys Gly Tyr Gln Val Arg Lys Asn
    50                  55                  60

Ser Glu Arg Ala Ser Arg Ile Glu Trp Glu His Val Val Pro Ala Trp
65                  70                  75                  80
```

```
Ser Phe Gly His Gln Arg Gln Cys Trp Gln Asp Gly Gly Arg Lys Asn
                85                  90                  95

Cys Val Lys Asp Pro Val Tyr Arg Arg Met Glu Ser Asp Leu His Asn
            100                 105                 110

Leu Gln Pro Ala Ile Gly Glu Val Asn Gly Asp Arg Gly Asn Phe Met
        115                 120                 125

Tyr Gly Gln Trp Ser Gly Gly Glu Gln Gln Tyr Gly Gln Cys Ala Met
    130                 135                 140

Lys Val Asp Phe Lys Asn Lys Leu Ala Glu Pro Ala Arg Ala Arg
145                 150                 155                 160

Gly Ala Ile Ala Arg Thr Trp Phe Tyr Met Arg Asp Gln Tyr Gln Leu
                165                 170                 175

Ser Met Ser Lys Gln Gln Thr Gln Leu Met Thr Ala Trp Ser Lys Leu
            180                 185                 190

Tyr Pro Val Thr Pro Trp Glu Cys Glu Arg Asp Arg Ile Ala Arg
        195                 200                 205

Val Gln Gly Asn His Asn Pro Tyr Val Gln Gln Ala Cys Gln Arg
    210                 215                 220
```

<210> SEQ ID NO 18
<211> LENGTH: 213
<212> TYPE: PRT
<213> ORGANISM: Yersinia sp.

<400> SEQUENCE: 18

```
His Gly Ile Asn Asn Phe Ser Gln Ala Lys Ala Val Ala Ala Lys Ile
1               5                   10                  15

His Gln Asp Ala Pro Gly Ser Phe Tyr Cys Gly Cys Gln Ile Asp Trp
            20                  25                  30

Gln Gly Lys Lys Gly Ile Pro Asp Leu Asn Ser Cys Gly Tyr Gln Pro
        35                  40                  45

Arg Lys Asn Ala Ala Arg Ala Ala Arg Ile Glu Trp Glu His Val Val
    50                  55                  60

Pro Ala Trp Gln Phe Gly His Gln Arg Gln Cys Trp Gln Gln Gly Gly
65                  70                  75                  80

Arg Lys Asn Cys Ala Lys Asp Pro Val Tyr Arg Gln Ile Glu Thr Asp
                85                  90                  95

Leu His Asn Leu Gln Pro Ala Ile Gly Glu Val Asn Gly Asp Arg Asn
            100                 105                 110

Asn Phe Met Tyr Ser Gln Trp Asn Gly Gly Ser Gly Gln Tyr Gly Gln
        115                 120                 125

Cys Ala Met Lys Val Asp Phe Lys Asn Lys Leu Ala Glu Pro Val
    130                 135                 140

Arg Ala Arg Gly Ala Ile Ala Arg Thr Tyr Phe Tyr Met Arg Asp Gln
145                 150                 155                 160

Tyr Gln Leu Arg Leu Ser Ser Gln Gln Ser Lys Leu Phe Gly Val Trp
                165                 170                 175

Asp Arg Gln Tyr Pro Val Thr Asp Trp Glu Cys Leu Arg Asp Glu Arg
            180                 185                 190

Ile Ala Lys Thr Gln Gly Asn His Asn Pro Tyr Val Gln Arg Ala Cys
        195                 200                 205

Gln Arg Pro Lys Ser
    210
```

<210> SEQ ID NO 19

```
<211> LENGTH: 213
<212> TYPE: PRT
<213> ORGANISM: Serratia sp.

<400> SEQUENCE: 19

His Gly Ile Asn Asn Phe Ser Gln Ala Lys Ala Ala Ala Lys Ile
1               5                   10                  15

Asn Gln Asp Ala Pro Gly Ser Phe Tyr Cys Gly Cys Lys Ile Asn Trp
            20                  25                  30

His Gly Lys Lys Gly Leu Pro Asp Leu Asn Ala Cys Gly Tyr Gln Pro
        35                  40                  45

Arg Lys Asn Ala Gln Arg Ala Gly Arg Ile Glu Trp Glu His Val Val
    50                  55                  60

Pro Ala Trp Gln Phe Gly His Gln Leu Gln Cys Trp Gln Asp Gly Gly
65                  70                  75                  80

Arg Lys Asn Cys Asn Arg Asp Pro Val Tyr Arg Gln Ile Glu Thr Asp
                85                  90                  95

Leu His Asn Leu Gln Pro Ala Ile Gly Glu Val Asn Gly Asp Arg Asn
            100                 105                 110

Asn Phe Met Tyr Ser Gln Trp Arg Gly Gly Glu Gly Gln Tyr Gly Gln
        115                 120                 125

Cys Pro Met Lys Val Asp Phe Lys His Lys Gln Ala Glu Pro Pro Ala
130                 135                 140

Arg Ala Arg Gly Ala Ile Ala Arg Thr Tyr Phe Tyr Met Arg Asp Arg
145                 150                 155                 160

Tyr His Leu Arg Leu Ser Arg Gln Gln Thr Gln Leu Phe Glu Val Trp
                165                 170                 175

Asn Arg Gln Tyr Pro Val Ser Gln Trp Glu Cys Gln Arg Glu Ala Arg
            180                 185                 190

Ile Ala Lys Val Gln Gly Asn Arg Asn Pro Tyr Ile Gln Gln Ala Cys
        195                 200                 205

Gln Arg Gln Lys Gly
        210

<210> SEQ ID NO 20
<211> LENGTH: 213
<212> TYPE: PRT
<213> ORGANISM: Pseudomonas sp.

<400> SEQUENCE: 20

Ala Gln Ala Gln Ala Pro Arg Thr Phe Ser Glu Ala Lys Lys Val Ala
1               5                   10                  15

Trp Gly Leu Tyr Ala Pro Gln Ser Thr Glu Phe Tyr Cys Gly Cys Lys
            20                  25                  30

Tyr Thr Gly Lys Arg Val Asp Leu Ala Gly Cys Gly Tyr Val Pro Arg
        35                  40                  45

Lys Ser Ala Lys Arg Ala Ser Arg Ile Glu Trp Glu His Ile Val Pro
    50                  55                  60

Ala Trp Gln Ile Gly His Leu Arg Gln Cys Trp Gln Asn Gly Gly Arg
65                  70                  75                  80

Lys Asn Cys Thr Lys Ser Asp Pro Val Tyr Lys Arg Ala Glu Ala Asp
                85                  90                  95

Leu His Asn Leu Val Pro Ser Ile Gly Glu Val Asn Gly Asp Arg Ser
            100                 105                 110

Asn Phe Ser Phe Gly Trp Val Pro Glu Gln Lys Gly Gly Tyr Gly Ser
        115                 120                 125
```

```
Cys Leu Thr Gln Val Asp Phe Lys Ala Lys Val Met Pro Arg Pro
        130                 135                 140

Ser Ile Arg Gly Met Ile Ala Arg Thr Tyr Phe Tyr Met Ser Lys Gln
145                 150                 155                 160

Tyr Asn Leu Arg Leu Ser Arg Gln Asp Gln Gln Leu Tyr Gln Ala Trp
                165                 170                 175

Asp Lys Thr Tyr Pro Pro Gln Ile Trp Glu Arg Gln Arg Asn Gln Gln
                180                 185                 190

Val Ala Cys Val Met Gly Arg Gly Asn Glu Phe Val Gly Pro Val Asp
            195                 200                 205

Leu Lys Ala Cys Lys
        210

<210> SEQ ID NO 21
<211> LENGTH: 213
<212> TYPE: PRT
<213> ORGANISM: Vibrio fischeri

<400> SEQUENCE: 21

Ala Pro Pro Ser Ser Phe Ser Lys Ala Lys Lys Glu Ala Val Lys Ile
1               5                   10                  15

Tyr Leu Asp His Pro Thr Ser Phe Tyr Cys Gly Cys Asp Ile Thr Trp
                20                  25                  30

Lys Asp Lys Lys Gly Ile Pro Asp Leu Gln Ser Cys Gly Tyr Asn
            35                  40                  45

Val Arg Lys Gln Glu Lys Arg Ala Ser Arg Ile Glu Trp Glu His Val
50                  55                  60

Val Pro Ala Trp Gln Phe Gly His Gln Arg Gln Cys Trp Gln Asp Gly
65                  70                  75                  80

Gly Arg Lys Asn Cys Thr Arg Lys Asp Lys Gln Phe Lys Leu Met Glu
                85                  90                  95

Ala Asp Leu His Asn Leu Val Pro Ala Ile Gly Glu Val Asn Gly Asp
                100                 105                 110

Arg Ser Asn Phe Arg Phe Ser Gln Trp Asn Gly Asn Lys Gly Ala Tyr
            115                 120                 125

Tyr Gly Gln Cys Ala Phe Lys Val Asp Phe Lys Gly Arg Val Ala Glu
130                 135                 140

Pro Pro Ala Gln Ser Arg Gly Ala Ile Ala Arg Thr Tyr Leu Tyr Met
145                 150                 155                 160

Asn Gln Glu Tyr Arg Phe Asn Leu Ser Lys Ser Gln Arg Gln Leu Met
                165                 170                 175

Asn Ala Trp Asp Lys Gln Tyr Pro Val Ser Glu Trp Glu Cys Glu Arg
                180                 185                 190

Asp Lys Arg Ile Ala Lys Ile Gln Gly Asn His Asn Gln Phe Val Tyr
            195                 200                 205

Lys Ala Cys Arg Lys
        210

<210> SEQ ID NO 22
<211> LENGTH: 213
<212> TYPE: PRT
<213> ORGANISM: Vibrio wodanis

<400> SEQUENCE: 22

Ala Pro Pro Ser Ser Phe Ser Lys Ala Lys Lys Leu Ala Val Lys Ile
1               5                   10                  15
```

Tyr Leu Asp His Pro Thr Ser Phe Tyr Cys Gly Cys Asp Ile Thr Trp
            20                  25                  30

Lys Asp Lys Lys Gly Ile Pro Asp Leu Glu Ser Cys Gly Tyr Glu
        35                  40                  45

Val Arg Lys Gln Glu Lys Arg Ala Ser Arg Ile Glu Trp Glu His Val
 50                  55                  60

Val Pro Ala Trp Gln Phe Gly His Gln Arg Gln Cys Trp Gln Asp Gly
 65                  70                  75                  80

Gly Arg Lys Asn Cys Thr Lys Asn Asp Lys Asn Phe Lys Met Met Glu
                85                  90                  95

Ala Asp Leu His Asn Leu Val Pro Ala Ile Gly Glu Val Asn Gly Asp
            100                 105                 110

Arg Ser Asn Phe Arg Phe Ser Gln Trp Asn Gly Ser Lys Gly Ala Asn
        115                 120                 125

Tyr Gly Gln Cys Ala Phe Lys Val Asp Phe Lys Gly Arg Val Ala Glu
130                 135                 140

Pro Pro Ala Gln Ser Arg Gly Ala Ile Ala Arg Thr Tyr Met Tyr Met
145                 150                 155                 160

Asn Lys Glu Tyr Arg Phe Asn Leu Ser Lys Ala Gln Arg Gln Leu Met
                165                 170                 175

Glu Ala Trp Asp Lys Gln Tyr Pro Val Ser Ala Trp Glu Cys Glu Arg
            180                 185                 190

Asp Gln Arg Ile Ala Lys Ile Gln Gly Asn His Asn Gln Phe Val Phe
        195                 200                 205

Lys Ala Cys Thr Lys
    210

<210> SEQ ID NO 23
<211> LENGTH: 212
<212> TYPE: PRT
<213> ORGANISM: Vibrio splendidus

<400> SEQUENCE: 23

Ala Pro Pro Ser Ser Phe Ser Lys Ala Lys Glu Ala Val Lys Ile
1               5                   10                  15

Tyr Leu Asp His Pro Thr Ser Phe Tyr Cys Gly Cys Asp Ile Thr Trp
            20                  25                  30

Lys Asp Lys Lys Gly Ile Pro Asp Leu Asp Gly Cys Gly Tyr Gln
        35                  40                  45

Val Arg Lys Gln Gln Lys Arg Ala Ser Arg Ile Glu Trp Glu His Val
 50                  55                  60

Val Pro Ala Trp Gln Phe Gly His Gln Arg Gln Cys Trp Gln Asp Gly
 65                  70                  75                  80

Gly Arg Lys Asn Cys Thr Arg Asn Asp Lys Val Phe Lys Ser Met Glu
                85                  90                  95

Ala Asp Leu His Asn Leu Thr Pro Ala Ile Gly Glu Val Asn Gly Asp
            100                 105                 110

Arg Ser Asn Tyr Asn Phe Ser Gln Trp Asn Ser Met Asp Gly Val Ser
        115                 120                 125

Tyr Gly Gln Cys Glu Met Gln Val Asn Phe Lys Gln Arg Lys Val Met
130                 135                 140

Pro Pro Asp Arg Ala Lys Gly Ser Ile Ala Arg Thr Tyr Leu Tyr Met
145                 150                 155                 160

Ser Gln Glu Tyr Gly Phe Lys Leu Ser Lys Gln Gln Thr Asn Leu Met

```
                    165                 170                 175
Met Ala Trp Asn Lys Gln Phe Pro Val Asn Glu Trp Glu Cys Thr Arg
            180                 185                 190

Asp Glu Arg Ile Phe Ala Ile Gln Gly Asn His Asn Pro Phe Val Tyr
        195                 200                 205

Gln Ala Cys Lys
    210

<210> SEQ ID NO 24
<211> LENGTH: 212
<212> TYPE: PRT
<213> ORGANISM: Vibrio harveyi

<400> SEQUENCE: 24

Ala Pro Pro Ser Ser Phe Ser Ala Ala Lys Arg Glu Ala Val Lys Ile
1               5                   10                  15

Tyr Ala Asp His Pro Thr Ser Phe Tyr Cys Gly Cys Asp Ile Lys Trp
            20                  25                  30

Gln Gly Lys Lys Gly Ile Pro Asp Leu Ala Ser Cys Gly Tyr Gln Val
        35                  40                  45

Arg Lys Gln Glu Lys Arg Ala Ser Arg Ile Glu Trp Glu His Val Val
    50                  55                  60

Pro Ala Trp Gln Phe Gly His Gln Arg Gln Cys Trp Gln Asn Gly Gly
65                  70                  75                  80

Arg Lys Asn Cys Thr Arg Asn Asp Asn Val Phe Lys Ser Met Glu Ala
                85                  90                  95

Asp Leu His Asn Leu Thr Pro Ala Ile Gly Glu Val Asn Gly Asp Arg
            100                 105                 110

Ser Asn Tyr Asn Phe Ser Gln Trp Asn Gly Met Asp Gly Val Ser Tyr
        115                 120                 125

Gly Arg Cys Glu Met Gln Val Asn Phe Lys Gln Arg Lys Val Met Pro
    130                 135                 140

Pro Asp Arg Ala Arg Gly Ser Ile Ala Arg Thr Tyr Leu Tyr Met Ser
145                 150                 155                 160

Lys Glu Tyr Gly Phe Lys Leu Ser Lys Gln Thr Gln Leu Met Ser
                165                 170                 175

Ala Trp Asn Lys Ser Tyr Pro Val Asp Lys Trp Glu Cys Glu Arg Asp
            180                 185                 190

Glu Arg Ile Ala Lys Ile Gln Gly Asn His Asn Pro Phe Val Gln Glu
        195                 200                 205

Ala Cys Arg Ala
    210

<210> SEQ ID NO 25
<211> LENGTH: 212
<212> TYPE: PRT
<213> ORGANISM: Vibrio rotiferianus

<400> SEQUENCE: 25

Ala Pro Pro Ser Ser Phe Ser Ala Ala Lys Arg Glu Ala Val Lys Ile
1               5                   10                  15

Tyr Ala Asp His Pro Thr Ser Phe Tyr Cys Gly Cys Asp Ile Lys Trp
            20                  25                  30

Gln Gly Lys Lys Gly Val Pro Asp Leu Ala Ser Cys Gly Tyr Gln Val
        35                  40                  45

Arg Lys Gln Glu Lys Arg Ala Ser Arg Ile Glu Trp Glu His Val Val
```

```
        50                  55                  60
Pro Ala Trp Gln Phe Gly His Gln Arg Gln Cys Trp Gln Asn Gly Gly
 65                  70                  75                  80

Arg Lys Asn Cys Thr Arg Asn Asp Lys Val Phe Lys Ser Met Glu Ala
                 85                  90                  95

Asp Leu His Asn Leu Thr Pro Ala Ile Gly Glu Val Asn Gly Asp Arg
                100                 105                 110

Ser Asn Tyr Asn Phe Ser Gln Trp Asn Gly Met Asp Gly Val Ser Tyr
                115                 120                 125

Gly Arg Cys Glu Met Gln Val Asn Phe Lys Gln Arg Lys Val Met Pro
            130                 135                 140

Pro Asp Arg Ala Arg Gly Ser Ile Ala Arg Thr Tyr Leu Tyr Met Ser
145                 150                 155                 160

Lys Glu Tyr Gly Phe Lys Leu Ser Lys Gln Thr Gln Leu Met Ser
                165                 170                 175

Ala Trp Asn Lys Thr Tyr Pro Val Asp Lys Trp Glu Cys Glu Arg Asp
                180                 185                 190

Glu Arg Ile Ala Lys Ile Gln Gly Asn His Asn Pro Phe Val Gln Glu
            195                 200                 205

Ala Cys Arg Ala
            210

<210> SEQ ID NO 26
<211> LENGTH: 213
<212> TYPE: PRT
<213> ORGANISM: Vibrio tubiashii

<400> SEQUENCE: 26

Ala Pro Pro Ser Ser Phe Ser Lys Ala Lys Lys Glu Ala Val Lys Ile
  1               5                  10                  15

Tyr Ala Asp His Pro Thr Ser Phe Tyr Cys Gly Cys Asn Ile Ser Trp
                 20                  25                  30

Gln Gly Arg Lys Gly Ile Pro Asp Leu Glu Ser Cys Gly Tyr Gln Val
             35                  40                  45

Arg Lys Gln Gln Lys Arg Ala Ser Arg Ile Glu Trp Glu His Val Val
 50                  55                  60

Pro Ala Trp Gln Phe Gly His Gln Arg Gln Cys Trp Gln Asn Gly Gly
 65                  70                  75                  80

Arg Lys Asn Cys Thr Lys Asn Asp Lys Ala Phe Arg Met Met Glu Ala
                 85                  90                  95

Asp Leu His Asn Leu Thr Pro Ala Ile Gly Glu Val Asn Gly Asp Arg
                100                 105                 110

Ser Asn Tyr Asn Phe Ser Gln Trp Asn Gly Ile Asp Gly Val Ser Tyr
                115                 120                 125

Gly Arg Cys Glu Met Gln Val Asn Phe Lys His Arg Lys Val Met Pro
            130                 135                 140

Pro Asp Arg Ala Lys Gly Ser Ile Ala Arg Thr Tyr Leu Tyr Met Ser
145                 150                 155                 160

Gln Glu Tyr Gly Phe Arg Leu Ser Lys Gln Gln Thr Gln Leu Met Asn
                165                 170                 175

Ala Trp Asn Lys Gln Phe Pro Val Asp His Trp Glu Cys Glu Arg Glu
                180                 185                 190

Gln Arg Ile Phe Lys Val Gln Gly Asn His Asn Pro Phe Val His Gln
            195                 200                 205
```

```
Ala Cys Gln Ala Leu
    210
```

<210> SEQ ID NO 27
<211> LENGTH: 204
<212> TYPE: PRT
<213> ORGANISM: Vibrio sinaloensis

<400> SEQUENCE: 27

```
Ala Pro Pro Ser Ser Phe Ser Lys Ala Lys Lys Glu Ala Ile Lys Ile
1               5                   10                  15

Tyr Ala Asp His Pro Ser Ser Phe Tyr Cys Gly Cys Asp Ile Thr Trp
            20                  25                  30

Gln Gly Arg Lys Gly Thr Pro Asp Leu Asn Ser Cys Gly Tyr Gln Val
        35                  40                  45

Arg Lys Gln Glu Lys Arg Ala Ser Arg Ile Glu Trp Glu His Val Val
    50                  55                  60

Pro Ala Trp Gln Phe Gly His Gln Arg Gln Cys Trp Gln Asn Gly Gly
65                  70                  75                  80

Arg Lys Asn Cys Ser Lys Asn Asp Asn Val Phe Arg Ser Met Glu Ala
                85                  90                  95

Asp Leu His Asn Leu Thr Pro Ala Ile Gly Glu Val Asn Gly Asp Arg
            100                 105                 110

Ser Asn Tyr Asn Phe Ser Gln Trp Asn Gly Val Asp Gly Val Ser Tyr
        115                 120                 125

Gly Arg Cys Glu Met Gln Val Asn Phe Lys Gln Arg Lys Val Met Pro
    130                 135                 140

Pro Asp Arg Ala Lys Gly Ser Ile Ala Arg Thr Tyr Leu Tyr Met Ser
145                 150                 155                 160

Lys Glu Tyr Gly Phe Lys Leu Ser Lys Gln Thr Gln Leu Met Thr
                165                 170                 175

Ala Trp Asn Lys Gln Phe Pro Val Asp Glu Trp Glu Cys Glu Arg Asp
            180                 185                 190

Lys Arg Ile Phe Lys Val Gln Gly Asn His Asn Pro
        195                 200
```

<210> SEQ ID NO 28
<211> LENGTH: 213
<212> TYPE: PRT
<213> ORGANISM: Vibrio vulnificus

<400> SEQUENCE: 28

```
Ala Pro Pro Ser Ser Phe Ser Ala Ala Lys Gln Ala Val Lys Ile
1               5                   10                  15

Tyr Gln Asp His Pro Ile Ser Phe Tyr Cys Gly Cys Asp Ile Glu Trp
            20                  25                  30

Gln Gly Lys Lys Gly Ile Pro Asn Leu Glu Thr Cys Gly Tyr Gln Val
        35                  40                  45

Arg Lys Gln Gln Thr Arg Ala Ser Arg Ile Glu Trp Glu His Val Val
    50                  55                  60

Pro Ala Trp Gln Phe Gly His Gln Arg Gln Cys Trp Gln Lys Gly Gly
65                  70                  75                  80

Arg Lys Asn Cys Ser Lys Asn Asp Gln Gln Phe Arg Leu Met Glu Ala
                85                  90                  95

Asp Leu His Asn Leu Thr Pro Ala Ile Gly Glu Val Asn Gly Asp Arg
            100                 105                 110
```

Ser Asn Phe Asn Phe Ser Gln Trp Asn Gly Met Asp Gly Val Ser Tyr
            115                 120                 125

Gly Arg Cys Glu Met Gln Val Asn Phe Lys Arg Lys Val Met Pro
        130                 135                 140

Pro Asp Arg Ala Arg Gly Ser Ile Ala Arg Thr Tyr Leu Tyr Met Ser
145                 150                 155                 160

Gln Glu Tyr Gly Phe Gln Leu Ser Lys Gln Gln Gln Leu Met Gln
                165                 170                 175

Ala Trp Asn Lys Ser Tyr Pro Val Asp Glu Trp Glu Cys Thr Arg Asp
                180                 185                 190

Asp Arg Ile Ala Lys Ile Gln Gly Asn His Asn Pro Phe Val Gln Gln
                195                 200                 205

Ser Cys Thr Val Arg
    210

<210> SEQ ID NO 29
<211> LENGTH: 211
<212> TYPE: PRT
<213> ORGANISM: Vibrio furnissii

<400> SEQUENCE: 29

Ala Pro Ala Ser Phe Ser Gln Ala Lys Arg Glu Ala Val Lys Ile Tyr
1               5                   10                  15

Gln Asp His Pro Val Thr Phe Tyr Cys Gly Cys Asp Ile Gln Trp Gln
                20                  25                  30

Gly Lys Lys Gly Thr Pro Asp Leu Lys Gly Cys Gly Tyr Gln Val Arg
            35                  40                  45

Lys Gln Glu Lys Arg Ala Ser Arg Ile Glu Trp Glu His Val Val Pro
50                  55                  60

Ala Trp Gln Phe Gly His Gln Leu Gln Cys Trp Gln Gln Gly Gly Arg
65                  70                  75                  80

Lys Gln Cys Ser Arg His Asp Thr Ala Phe Lys Arg Met Glu Ala Asp
                85                  90                  95

Leu His Asn Leu Thr Pro Ala Ile Gly Glu Val Asn Gly Asp Arg Ser
                100                 105                 110

Asn Leu Asn Phe Ser Gln Trp His Gly Ile Asp Gly Ala Thr Tyr Gly
            115                 120                 125

Gln Cys Glu Ile Gln Val Asn Phe Gln Gln Arg Lys Val Met Pro Pro
        130                 135                 140

Glu Arg Ala Arg Gly Ala Ile Ala Arg Thr Tyr Leu Tyr Met Ser Gln
145                 150                 155                 160

Glu Tyr Gly Phe Arg Leu Ser Lys Ser Gln Thr Gln Leu Met Gln Val
                165                 170                 175

Trp Asn Arg Gln Tyr Pro Val Asp Ser Trp Glu Cys Glu Arg Asp Gln
                180                 185                 190

Arg Ile Phe Lys Val Gln Gly Asn His Asn Pro Phe Val Arg Gln Gln
                195                 200                 205

Cys Ser Ser
    210

<210> SEQ ID NO 30
<211> LENGTH: 212
<212> TYPE: PRT
<213> ORGANISM: Vibrio anguillarum

<400> SEQUENCE: 30

-continued

```
Ala Pro Pro Ala Ser Phe Ser Gln Ala Lys Lys Glu Ala Leu Lys Ile
1               5                   10                      15

Tyr His Asp His Pro Val Ser Phe Tyr Cys Gly Cys Asp Ile Ala Trp
            20                  25                  30

Gln Gly Lys Lys Gly Thr Pro Asp Leu Gln Ala Cys Gly Tyr Gln Val
        35                  40                  45

Arg Lys Gln Gln Thr Arg Ala Ser Arg Ile Glu Trp Glu His Val Val
    50                  55                  60

Pro Ala Trp Gln Phe Gly His Gln Arg Gln Cys Trp Gln Gln Gly Gly
65                  70                  75                  80

Arg Lys Asn Cys Thr Lys Asn Asp Thr Ile Phe Arg Ser Met Glu Ala
            85                  90                  95

Asp Leu His Asn Leu Thr Pro Ala Ile Gly Glu Val Asn Gly Asp Arg
            100                 105                 110

Ser Asn Tyr Asn Phe Ser Gln Trp Asn Gly Val Glu Gly Glu Ser Tyr
            115                 120                 125

Gly Arg Cys Glu Met Gln Val Asp Phe Lys Gln Arg Lys Val Met Pro
        130                 135                 140

Pro Asp Arg Ala Arg Gly Ser Ile Ala Arg Thr Tyr Leu Tyr Met Ser
145                 150                 155                 160

Gln Asn Tyr Gly Phe Gln Leu Ser Lys Ser Gln Thr Gln Leu Met Gln
                165                 170                 175

Ala Trp Asn Arg Gln Tyr Pro Ala Asp Glu Trp Glu Cys Lys Arg Asp
            180                 185                 190

Gln Arg Ile Ala Lys Val Gln Gly Asn His Asn Pro Phe Val Gln Gln
            195                 200                 205

Gln Cys Arg Ser
        210
```